US010699057B2

(12) United States Patent
Lei et al.

(10) Patent No.: US 10,699,057 B2
(45) Date of Patent: Jun. 30, 2020

(54) SYSTEM AND METHOD FOR CONTROLLING INFORMATION PRESENTED TO USER REFERRING TO CONTENTS

(71) Applicant: HITACHI, LTD., Tokyo (JP)

(72) Inventors: Miaomei Lei, Tokyo (JP); Toshinori Miyoshi, Tokyo (JP); Yoshiki Niwa, Tokyo (JP); Hiroki Sato, Tokyo (JP)

(73) Assignee: HITACHI LTD., Tokyo (JP)

( * ) Notice: Subject to any disclaimer, the term of this patent is extended or adjusted under 35 U.S.C. 154(b) by 0 days.

(21) Appl. No.: 15/766,633

(22) PCT Filed: Oct. 7, 2015

(86) PCT No.: PCT/JP2015/078535
§ 371 (c)(1),
(2) Date: Apr. 6, 2018

(87) PCT Pub. No.: WO2017/060994
PCT Pub. Date: Apr. 13, 2017

(65) Prior Publication Data
US 2018/0285351 A1 Oct. 4, 2018

(51) Int. Cl.
*G06F 40/10* (2020.01)
*G16B 99/00* (2019.01)
(Continued)

(52) U.S. Cl.
CPC ............ *G06F 40/10* (2020.01); *A61B 5/4064* (2013.01); *G06F 40/253* (2020.01); (Continued)

(58) Field of Classification Search
None
See application file for complete search history.

(56) References Cited

U.S. PATENT DOCUMENTS

2011/0219304 A1* 9/2011 Nakano .................. G06F 17/21 715/705
2016/0203726 A1* 7/2016 Hibbs ...................... G09B 7/02 434/308

FOREIGN PATENT DOCUMENTS

JP 10-078743 A 3/1998
JP 10-207615 A 8/1998
(Continued)

OTHER PUBLICATIONS

International Search Report for WO 20171060994, dated Nov. 10, 2015.

*Primary Examiner* — Antim G Shah
(74) *Attorney, Agent, or Firm* — Volpe and Koenig, P.C.

(57) ABSTRACT

Provided is a system which controls information presented to a user referring to contents including a plurality of elements, outputs the contents to an output device, obtains bioinformation of the user at a time when each of the elements included in the contents is output to the output device, calculates an understanding level of the user with respect to each of the elements included in the contents, based on each piece of the obtained bioinformation, determines the understanding type based on the calculated understanding level and a difficulty level indicated by the difficulty level information of the elements of which the understanding level is equal to or lower than a first threshold value, in a case where it is determined that the user does not understand the contents based on the calculated understanding level, and outputs the presented information which corresponds to the determined understanding type to the output device.

13 Claims, 14 Drawing Sheets

(51) Int. Cl.

| | |
|---|---|
| ***A61B 5/00*** | (2006.01) |
| ***G16H 10/20*** | (2018.01) |
| ***G06F 40/47*** | (2020.01) |
| ***G06F 40/30*** | (2020.01) |
| ***G06F 40/253*** | (2020.01) |
| ***G06F 40/289*** | (2020.01) |
| *A61B 5/1455* | (2006.01) |

(52) U.S. Cl.
CPC ............ *G06F 40/289* (2020.01); *G06F 40/30* (2020.01); *G06F 40/47* (2020.01); *G16B 99/00* (2019.02); *G16H 10/20* (2018.01); *A61B 5/0075* (2013.01); *A61B 5/14553* (2013.01)

(56) References Cited

FOREIGN PATENT DOCUMENTS

| | | |
|---|---|---|
| JP | 2006-023566 A | 1/2006 |
| JP | 2011-150408 A | 8/2011 |
| JP | 2015-087782 A | 5/2015 |

* cited by examiner

[Fig. 1]
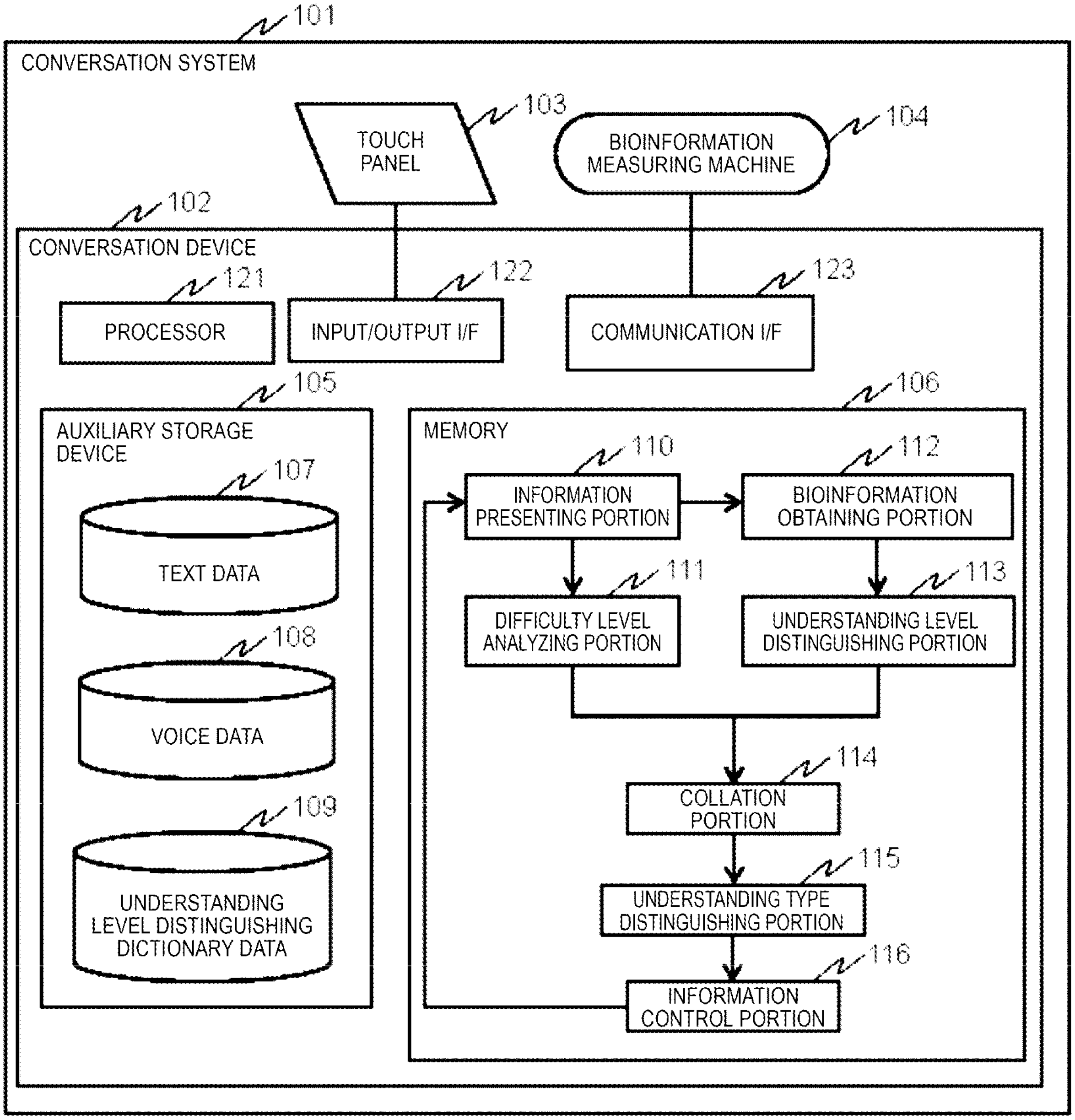

| | | |
|---|---|---|
| CONTENTS: NEWS, ENGLISH, BRAIN SCIENCE | | |
| BACKGROUND:<br>ENGLISH VERSION: Near-Infrared Spectroscopy (fNIR or fNIRS), is the use of NIRS (near-infrared spectroscopy) for the purpose of functional neuroimaging. Using fNIR, brain activity is measured through hemodynamic responses associated with neuron behavior......<br>JAPANESE VERSION: NIRSとは、近赤外光を用いて頭皮上から非侵襲的に脳機能マッピングする、「光機能画像法」の原理を応用した装置のことである。この技術はほかの脳機能計測技術と比べて、被験者に対する安全性が高く、拘束性が低い特徴がある。そのため、脳科学応用を実現するツールとして期待されている。<br>PICTURE:<br>...... | | |
| **Version1**: SIMPLE LEVEL<br>Near infrared spectroscopy (NIRS) is one type of measuring tools of brain. It uses infrared light to draw activation maps of the brain Not like fMRI, there is almost no restriction when using NIRS. So you can measure the brain activity at any position, even walking is OK. At the same time, any person can be measured by using NIRS, such as babies or patients. | **Version2**: INTERMEDIATE LEVEL<br>Near infrared spectroscopy (NIRS) based on the optical properties of hemoglobin, is also a hemodynamic based technique but reduces such restrictions of fMRI. In the case of NIRS, uses flexible optic fibers to carry NIR light to and from tissue, the hemodynamic responses in association with the brain activity can be topographically mapped on the brain surface. Optic fibers are suitable for any head position, thus NIRS measurements can be performed in a natural environment without restrictions like fMRI. Due to the less restriction, any population such as infants or patients can be measured in a comfortable environment. | **Version3**<br>... |
| WORDS<br>Restriction : anything that limits what you can do<br>...... | Optical : devices, processes, and effects involve or relate to vision, light, or images<br>...... | ...... |

201

202

203

204

[Fig. 3]
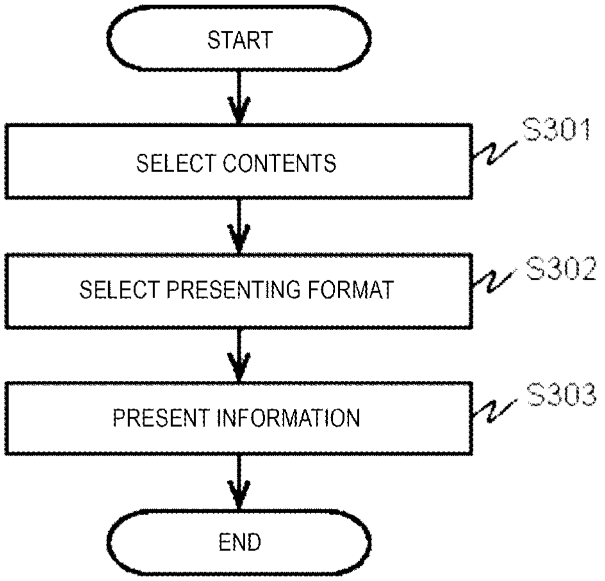
[Fig. 4]
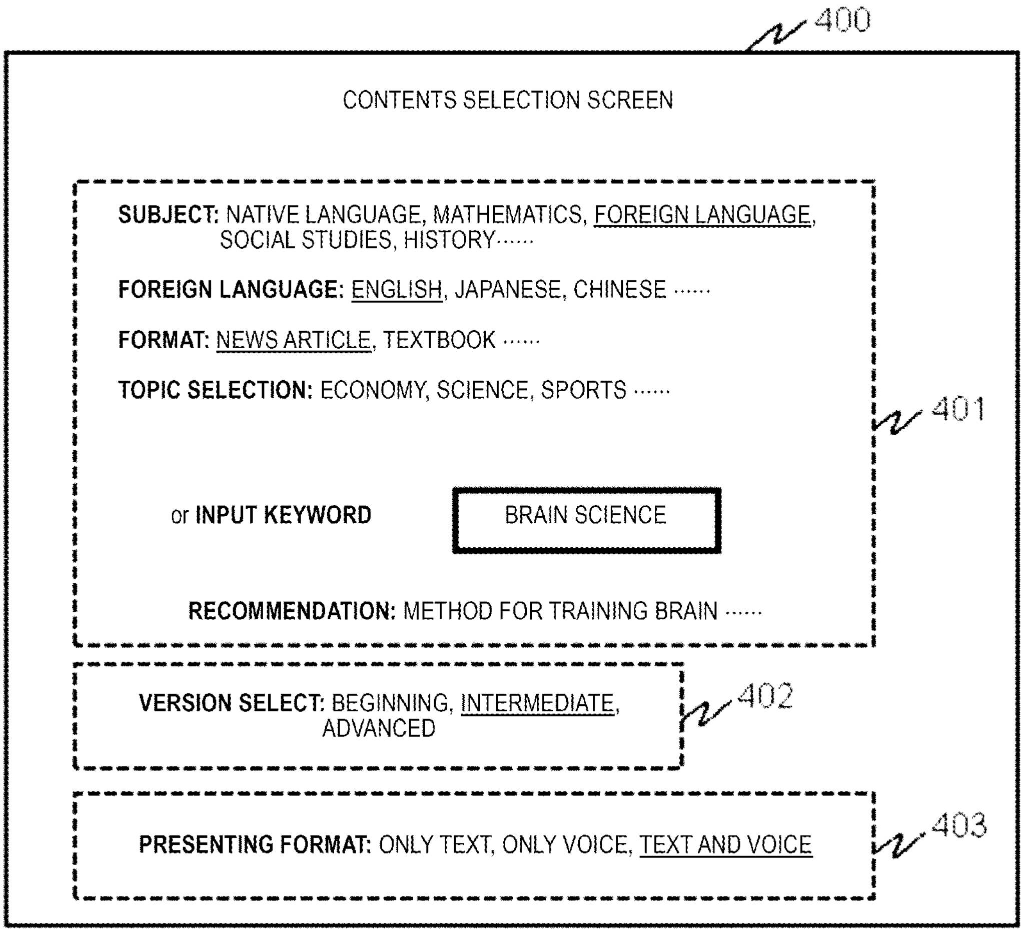

[Fig. 5]
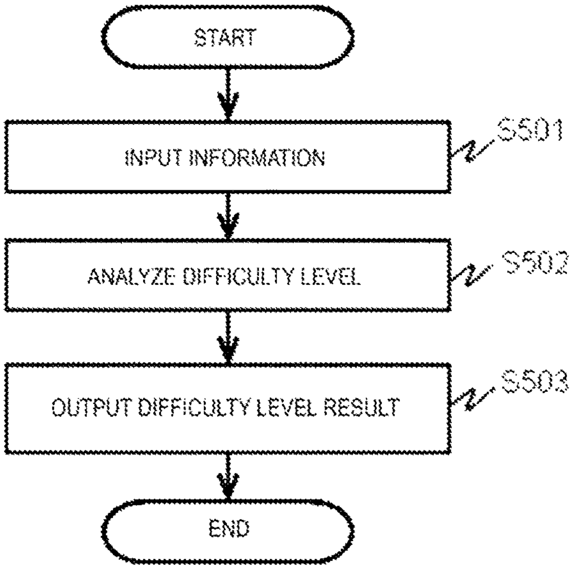
[Fig. 6]
600
| | | TEXT DATA | | | VOICE DATA | | |
|---|---|---|---|---|---|---|---|
| TIME | WORD | WORD DIFFICULTY LEVEL | SENTENCE STRUCTURE DIFFICULTY LEVEL | ... | SPEED DIFFICULTY LEVEL | ACCENT DIFFICULTY LEVEL | ... |
| t0 | Now | 0.2 | 0.4 | ... | 0.0 | 0.0 | ... |
| t1 | you | 0.1 | 0.4 | ... | 0.0 | 0.0 | ... |
| t2 | have | 0.2 | 0.4 | ... | 0.0 | 0.0 | ... |
| t3 | the | 0.1 | 0.4 | ... | 0.6 | 0.3 | ... |
| t4 | same | 0.3 | 0.4 | ... | 0.6 | 0.2 | ... |
| t5 | delicious | 0.6 | 0.4 | ... | 0.6 | 0.4 | ... |
| t6 | meals | 0.4 | 0.4 | ... | 0.8 | 0.0 | ... |
| ... | ... | ... | ... | ... | ... | ... | ... |
601 602 603 604 605 606

[Fig. 7]
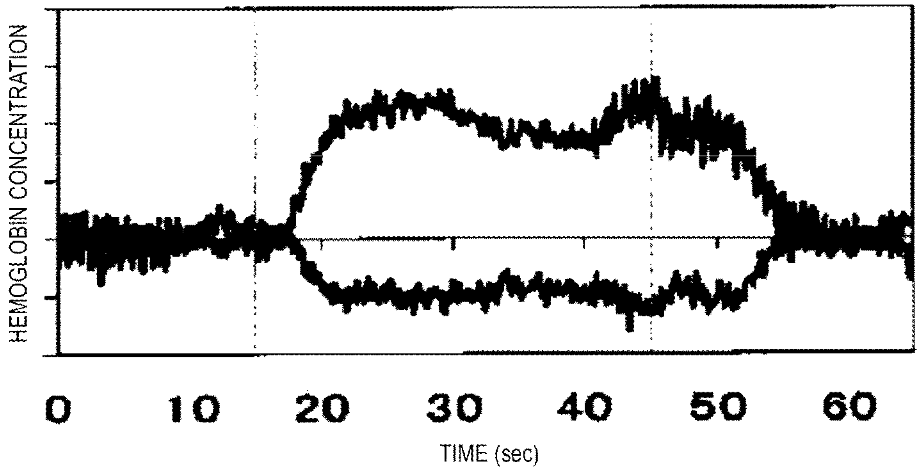
[Fig. 8]
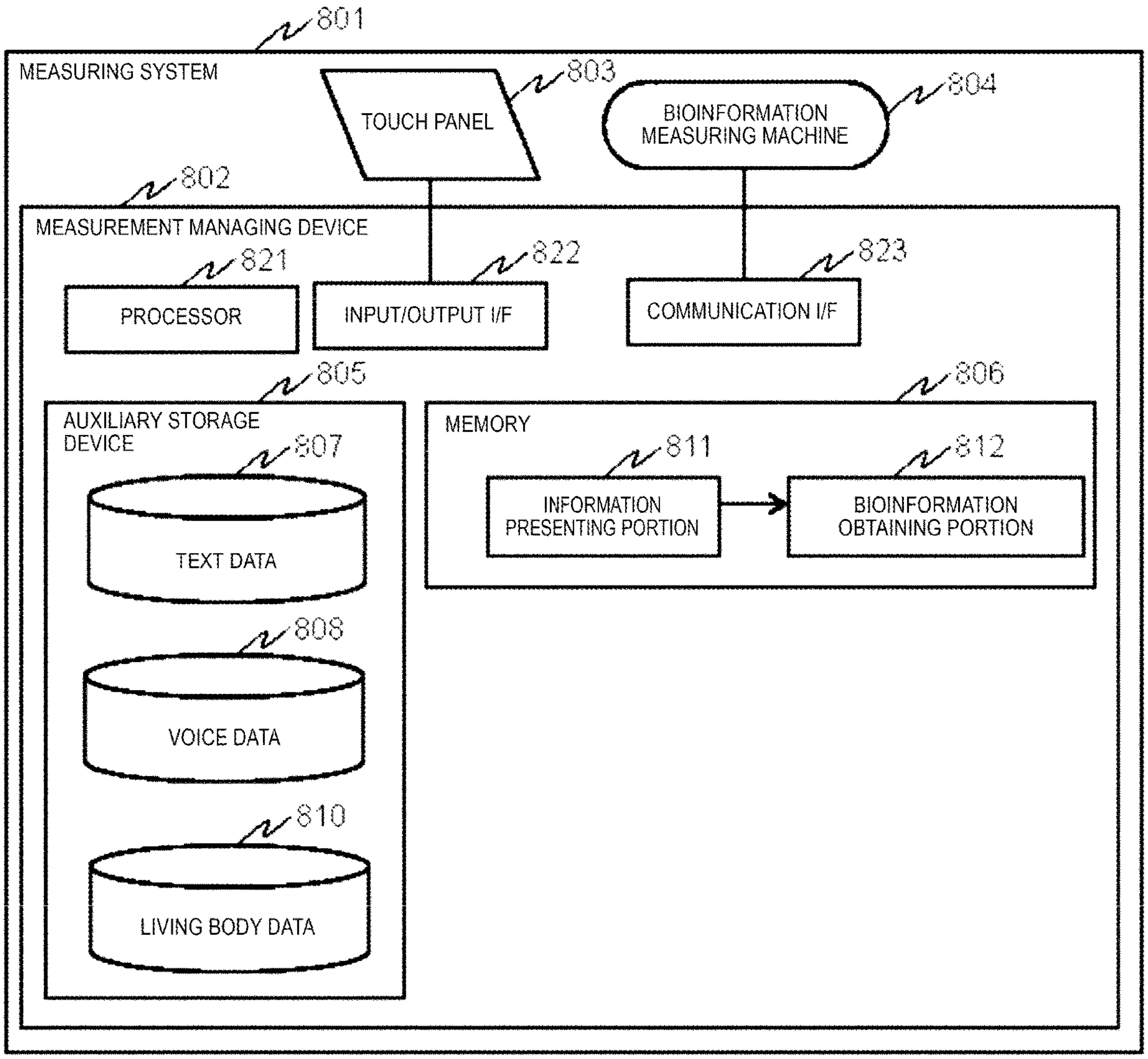

[Fig. 9]
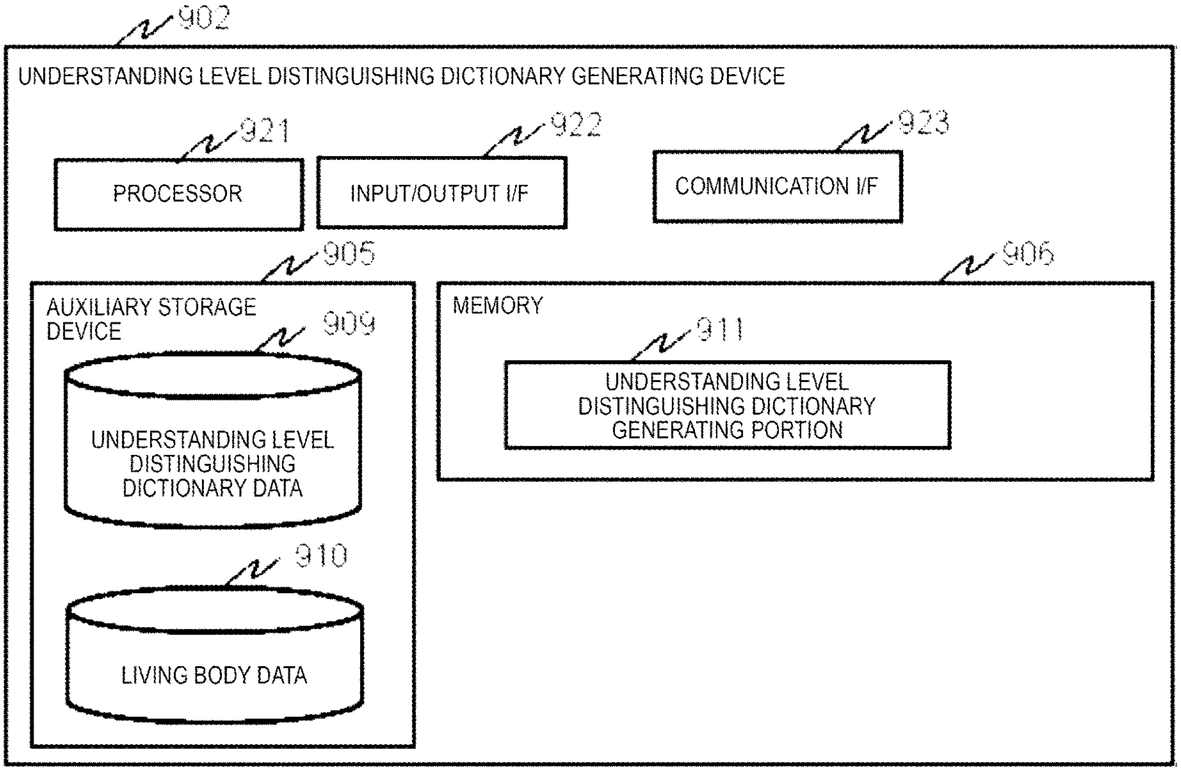
[Fig. 10]
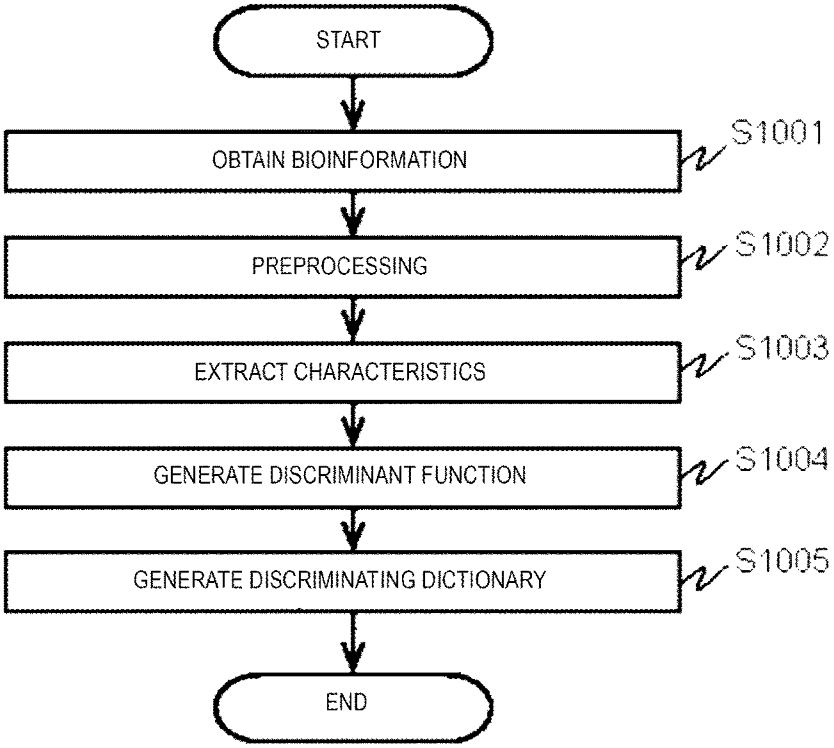

[Fig. 11]
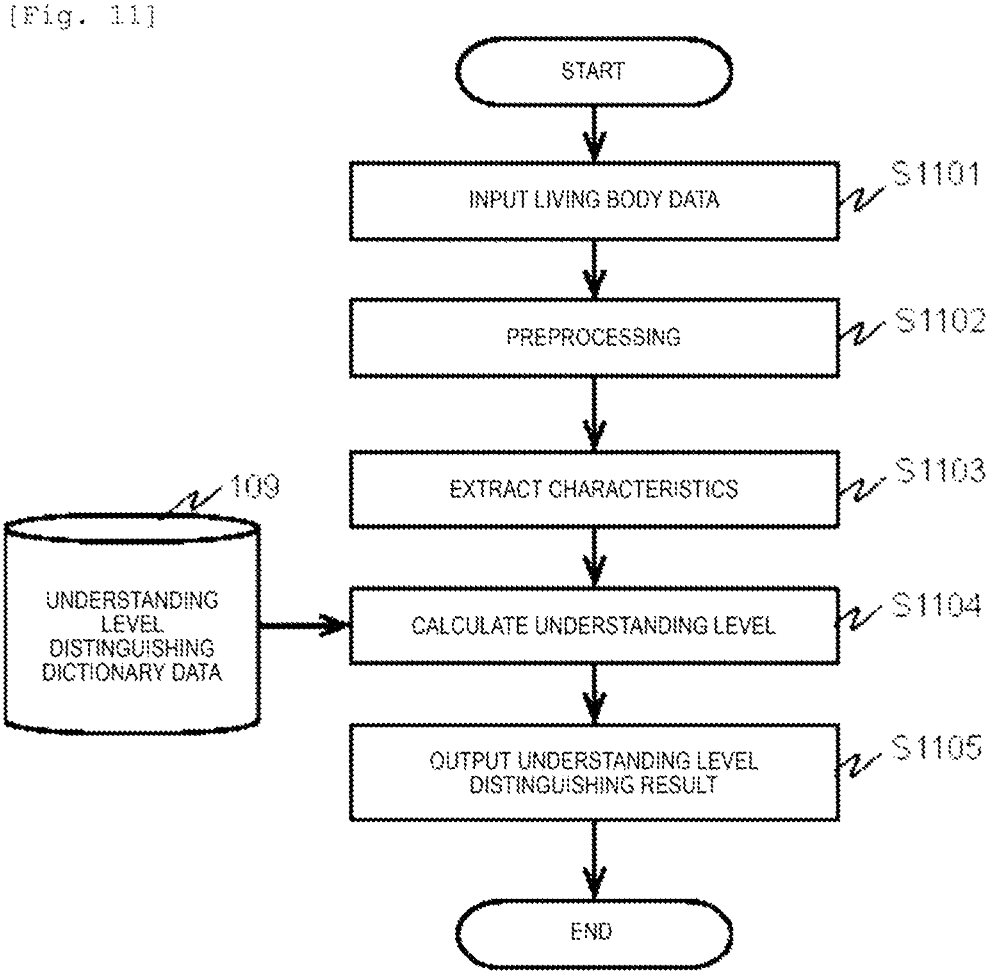
[Fig. 12]
| TIME | UNDERSTANDING LEVEL |
|---|---|
| t0 | 0.8 |
| t1 | 0.9 |
| t2 | 0.8 |
| t3 | 0.9 |
| t4 | 0.7 |
| t5 | 0.4 |
| t6 | 0.6 |
| ... | ... |

[Fig. 13]
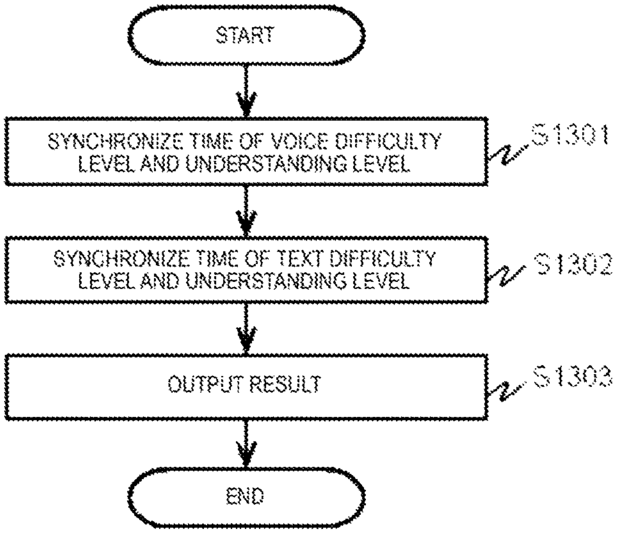
[Fig. 14]
| TIME | UNDERSTANDING LEVEL RESULT | WORD DIFFICULTY LEVEL | SENTENCE STRUCTURE DIFFICULTY LEVEL | SPEED DIFFICULTY LEVEL | ACCENT DIFFICULTY LEVEL | ... |
|---|---|---|---|---|---|---|
| t0 | 0.8 | 0.4 | 0.3 | 0.0 | 0.0 | ... |
| t1 | 0.9 | 0.4 | 0.3 | 0.0 | 0.0 | ... |
| t2 | 0.8 | 0.4 | 0.3 | 0.0 | 0.0 | ... |
| t3 | 0.9 | 0.4 | 0.3 | 0.6 | 0.3 | ... |
| t4 | 0.7 | 0.4 | 0.3 | 0.6 | 0.2 | ... |
| t5 | 0.4 | 0.4 | 0.2 | 0.6 | 0.4 | ... |
| t6 | 0.6 | 0.4 | 0.2 | 0.8 | 0.0 | ... |
| ... | ... | ... | ... | ... | ... | ... |

[Fig. 15]
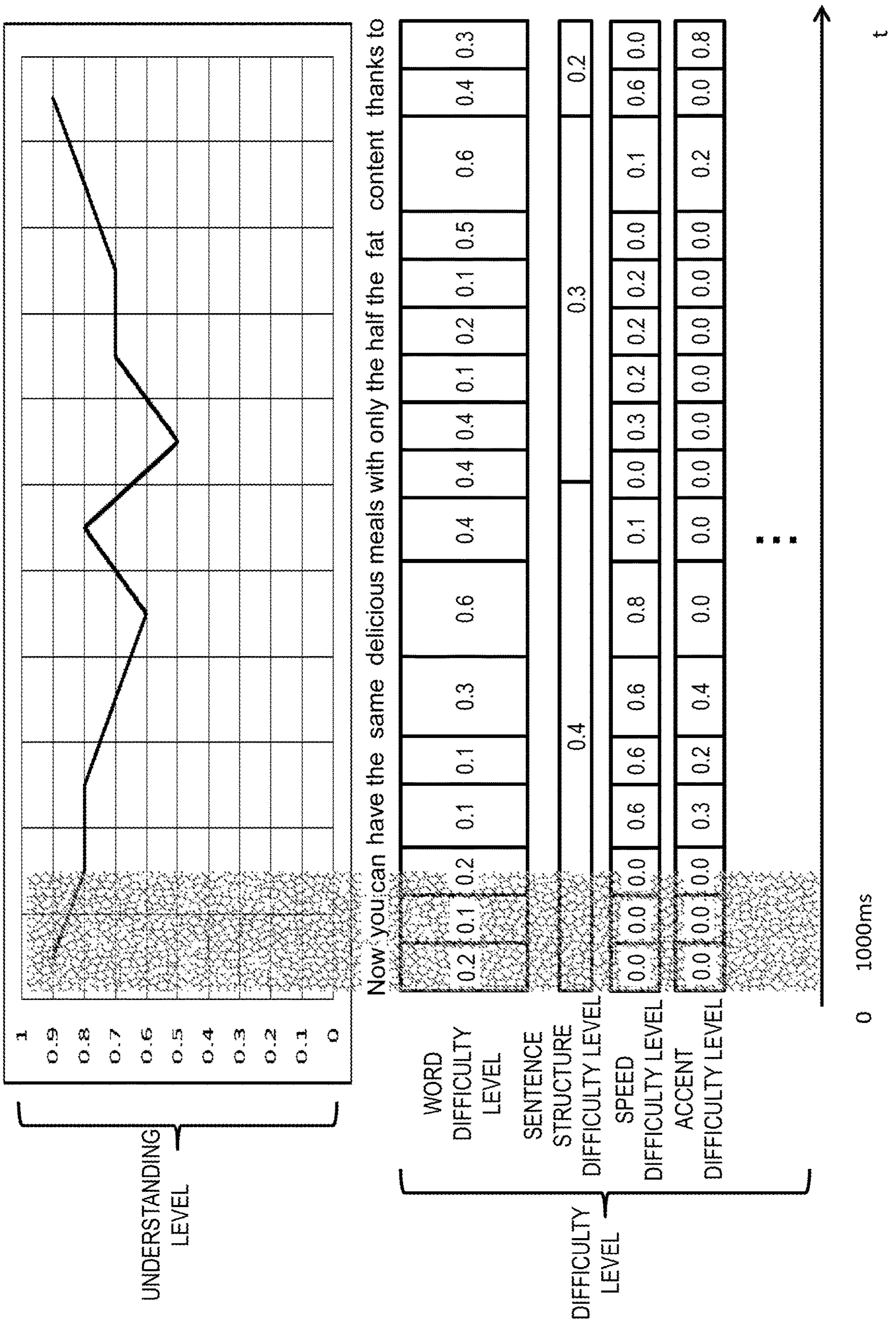

[Fig. 16]
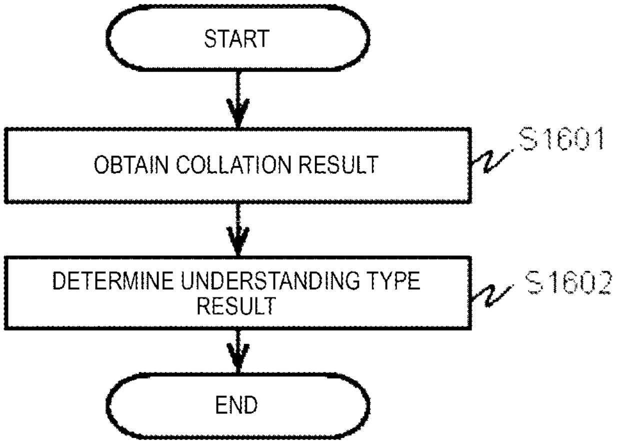
[Fig. 17]
| ITEMS THAT CANNOT BE UNDERSTOOD | RESULT |
|---|---|
| WORD | ○ |
| SENTENCE STRUCTURE | — |
| TOPIC | — |
| SPEED | — |
| ACCENT | — |
| ... | ... |

[Fig. 18]
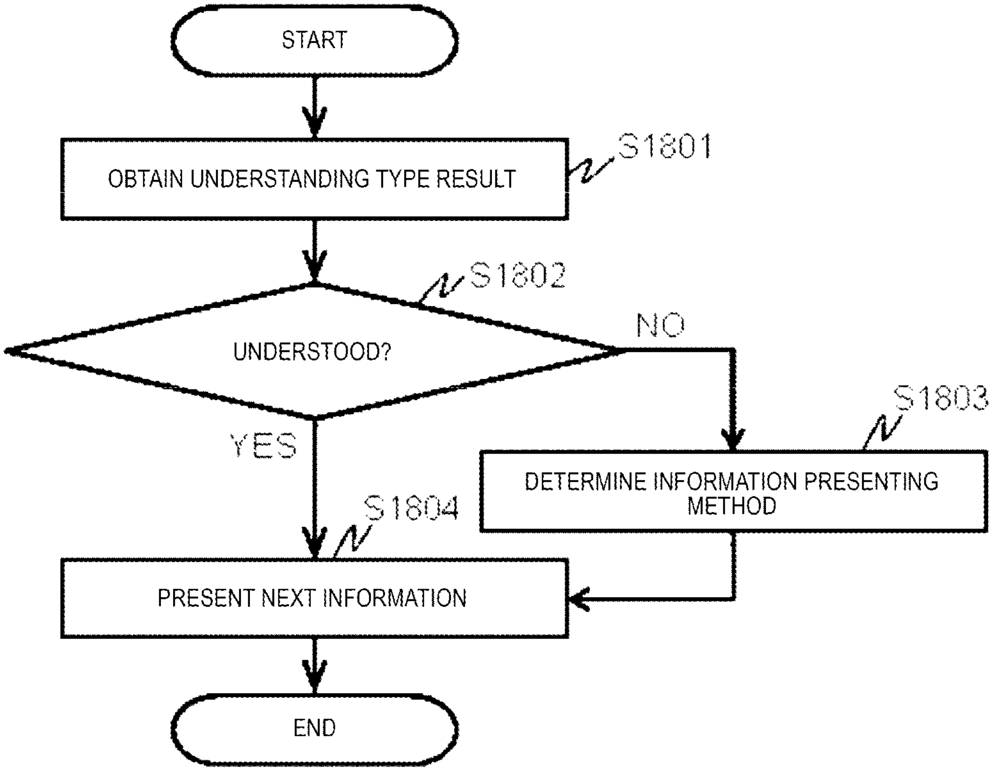
[Fig. 19]
| ITEMS THAT USER DOES NOT UNDERSTAND | CONTROL | CHOICE |
|---|---|---|
| WORD | REWORD BY SIMPLE WORDS OF WHICH NUMBER OF VOCABULARY WORDS IS 1000 OR LESS | ○ |
| SENTENCE STRUCTURE | REWORD BY SIMPLE SENTENCE STRUCTURE | |
| TOPIC | INTRODUCE BACKGROUND KNOWLEDGE | |
| SPEED | REWORD SLOWLY | |
| ACCENT | REWORD BY STANDARD LANGUAGE | |
| ... | ... | |

[Fig. 20]
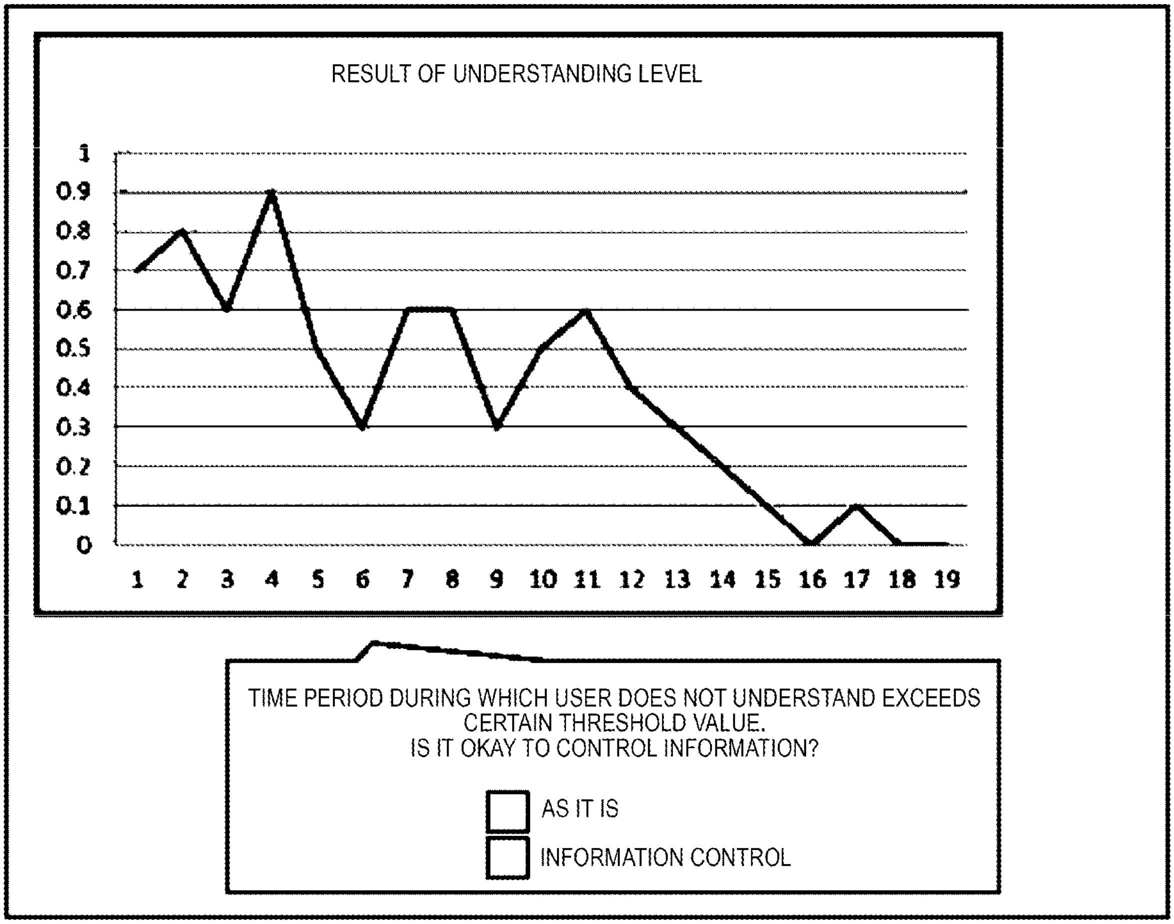

[Fig. 21A]
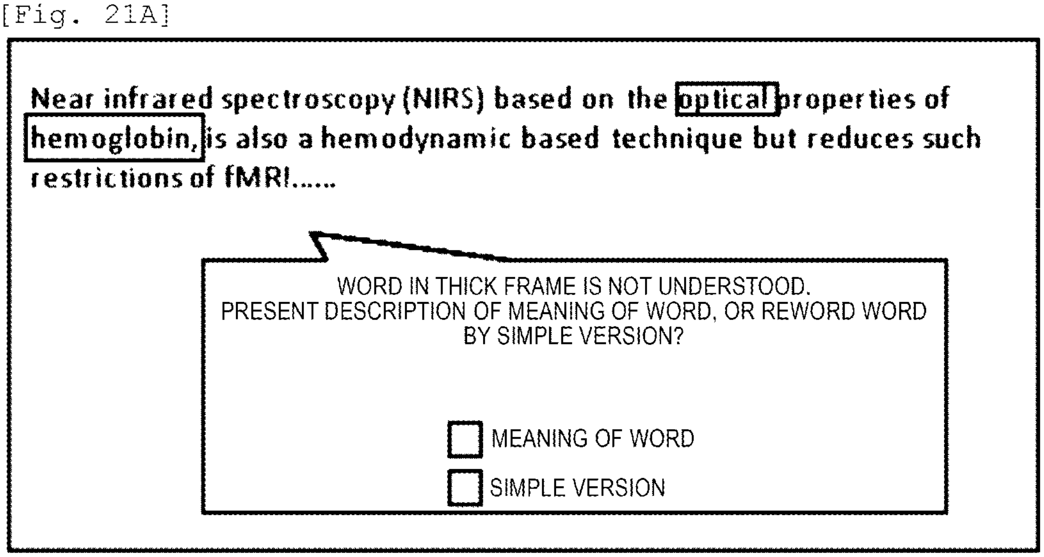
[Fig. 21B]
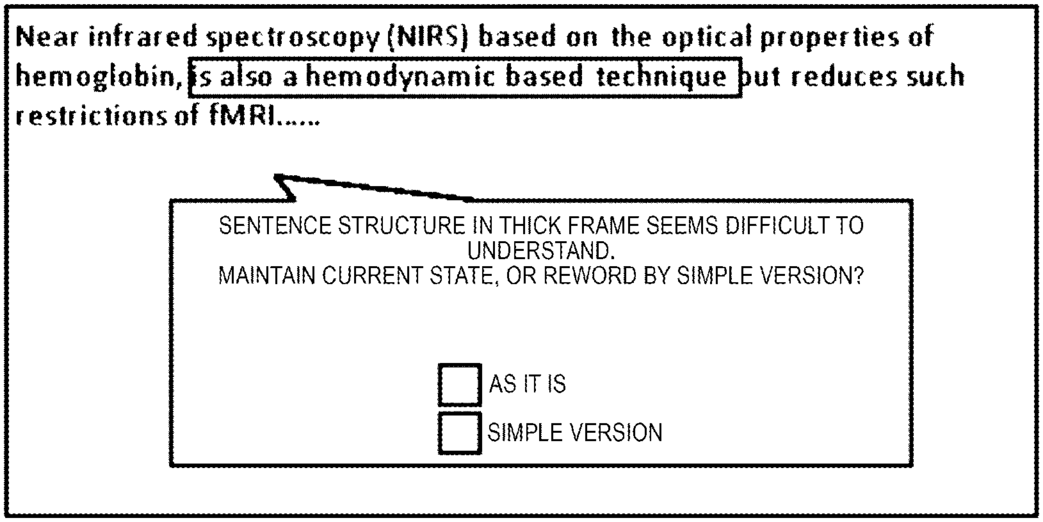

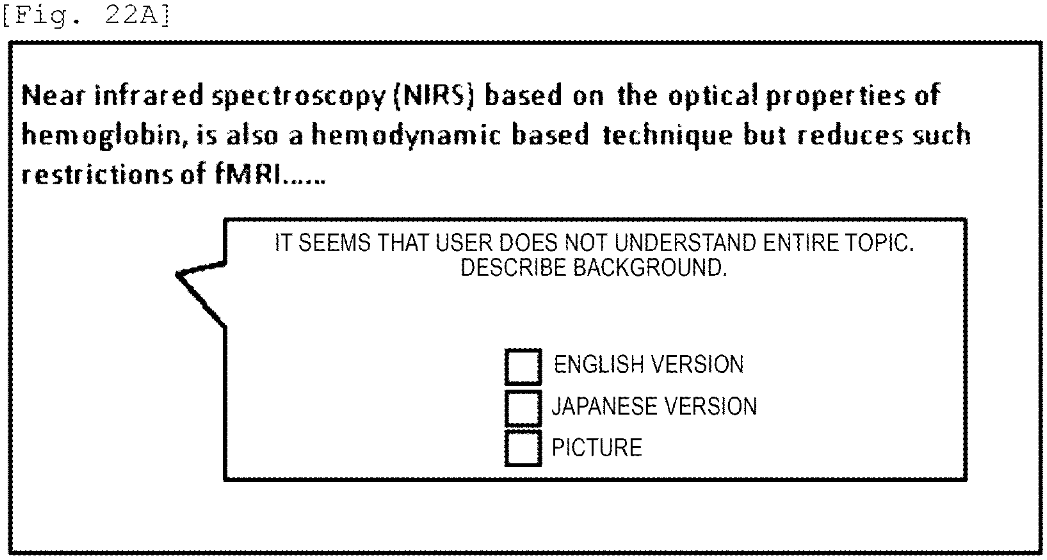

[Fig. 22A]

Near infrared spectroscopy (NIRS) based on the optical properties of hemoglobin, is also a hemodynamic based technique but reduces such restrictions of fMRI......

> IT SEEMS THAT USER DOES NOT UNDERSTAND ENTIRE TOPIC.
> DESCRIBE BACKGROUND.
>
> ☐ ENGLISH VERSION
> ☐ JAPANESE VERSION
> ☐ PICTURE

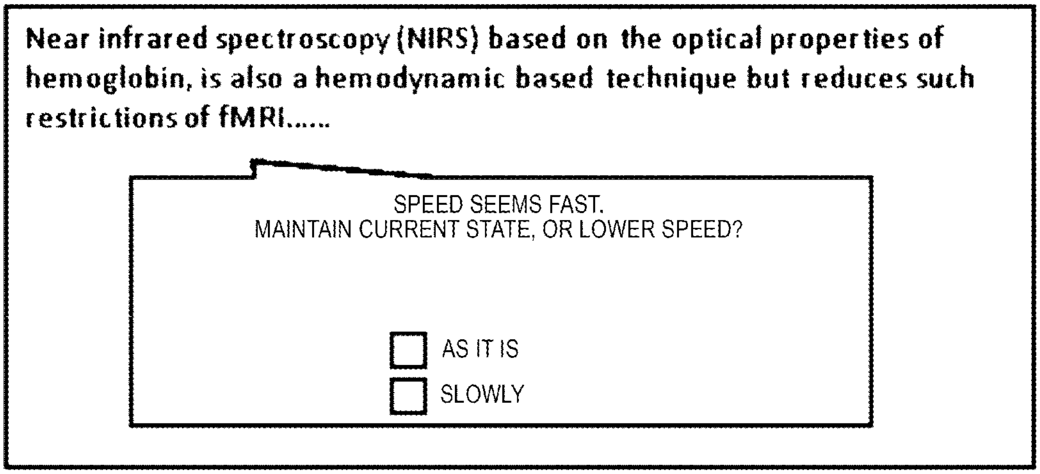

[Fig. 22B]

Near infrared spectroscopy (NIRS) based on the optical properties of hemoglobin, is also a hemodynamic based technique but reduces such restrictions of fMRI......

> SPEED SEEMS FAST.
> MAINTAIN CURRENT STATE, OR LOWER SPEED?
>
> ☐ AS IT IS
> ☐ SLOWLY

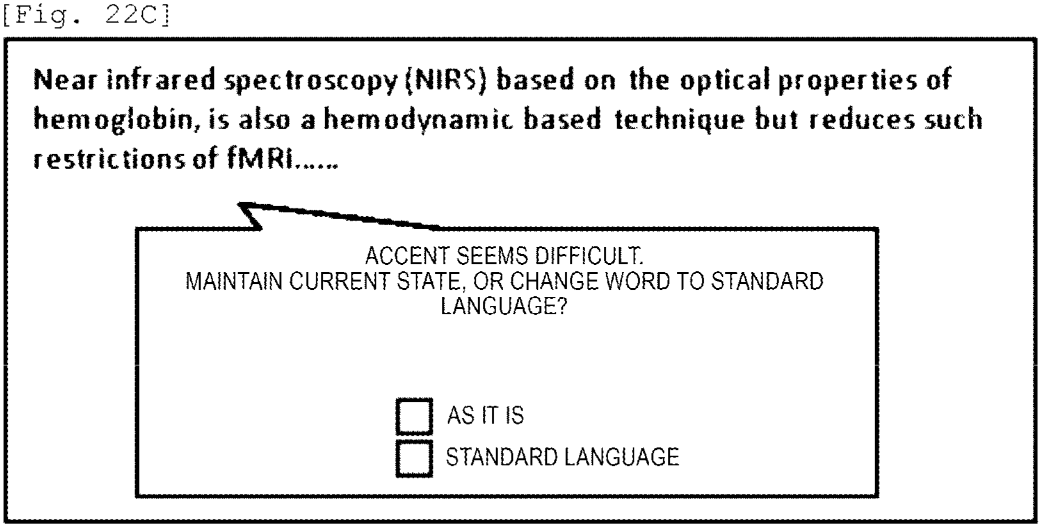

[Fig. 22C]

Near infrared spectroscopy (NIRS) based on the optical properties of hemoglobin, is also a hemodynamic based technique but reduces such restrictions of fMRI......

> ACCENT SEEMS DIFFICULT.
> MAINTAIN CURRENT STATE, OR CHANGE WORD TO STANDARD LANGUAGE?
>
> ☐ AS IT IS
> ☐ STANDARD LANGUAGE

SYSTEM AND METHOD FOR CONTROLLING INFORMATION PRESENTED TO USER REFERRING TO CONTENTS

TECHNICAL FIELD

The present invention relates to a system and a method for controlling information presented to a user referring to contents.

BACKGROUND ART

In recent years, as the technology for visualizing brain has been developed, not only fully realizing physiological knowledge about the brain but also assuming a state of a human from a brain measuring signal is performed.

Examples of a method for measuring a brain activity in a non-invasive manner include electroencephalogram measurement, functional magnetic resonance imaging (fMRI), magnetoencephalography, and near-infrared spectroscopy (NIRS).

As a background technology of the technological field, there is JP-A-2011-150408 (PTL 1). The application describes "In a work place where machines are used, a machine learning algorithm is employed to estimate an internal state (visual caution, working memory, a degree of skill or the like) which is obtained from a biometric signal of an operator. In addition, in a case of predicting and detecting a state where a human error is likely to occur, and estimating a state where a risk of making a mistake is high, the mistakes are prevented in advance by feeding back the state to the operator by means of the sense of sight, the sense of hearing, and the sense of touch or by a combination of the senses (refer to summary).

CITATION LIST

Patent Literature

PTL 1: JP-A-2011-150408

SUMMARY OF INVENTION

Technical Problem

In the technology described in PTL 1, a method for estimating the internal state from the biometric signal of the user is described, but it is not possible to specify the reason why the internal state is achieved, or to perform control for improving the internal state.

In other words, the technology described in PTL 1 can estimate an understanding level with respect to the information of the user from the biometric signal of the user referring to the presented information, but in a state where the understanding level is low, it is not possible to specify the reason why the user cannot understand the information. Otherwise, the technology described in PTL 1 cannot present the information that corresponds to the reason why it is not possible to understand the information.

In addition, for example, in many cases, it is difficult for the user himself or herself to specify the contents that the user cannot understand among the pieces of presented information, and the reason why the user cannot understand the information in a case where the understanding level of the user is low. Here, one aspect of the present invention specifies the objective understanding level of the user with respect to the presented information and the reason of a case where it is not possible to understand the information, and presents the information which corresponds to the understanding level and the reason.

Solution to Problem

One aspect of the present invention employs the following configuration. There is provided a system which controls information presented to a user referring to contents including a plurality of elements, including: a processor; a storage device; and an output device, in which the storage device includes the contents, difficulty level information that indicates difficulty levels of each of the plurality of elements, and presented information which corresponds to each understanding type that indicates the reason why the user cannot understand the contents, in which the processor outputs the contents to the output device, obtains bioinformation of the user at a time when each of the elements included in the contents is output to the output device, calculates an understanding level of the user with respect to each of the elements included in the contents, based on each piece of the obtained bioinformation, determines the understanding type based on the calculated understanding level and a difficulty level indicated by the difficulty level information of the elements of which the understanding level is equal to or lower than a first threshold value, in a case where it is determined that the user does not understand the contents based on the calculated understanding level, and outputs the presented information which corresponds to the determined understanding type to the output device.

Advantageous Effects of Invention

According to one aspect of the present invention, it is possible to specify the objective understanding level of the user with respect to presented information and the reason in a case where the user cannot understand the information, and to present the information which corresponds to the understanding level and the reason.

Problems, configurations, and effects other than those described above become apparent by the following description of the embodiments.

BRIEF DESCRIPTION OF DRAWINGS

FIG. 1 is a block diagram illustrating a configuration example of a conversation device in Example 1.

FIG. 2 is one example of a text included in text data in Example 1.

FIG. 3 is a flowchart illustrating one example of information presenting processing in Example 1.

FIG. 4 is one example of a contents selection screen in Example 1.

FIG. 5 is a flowchart illustrating one example of difficulty level analysis processing of presented information in Example 1.

FIG. 6 is one example of a difficulty level analysis result in Example 1.

FIG. 7 is one example of hemoglobin concentration data in Example 1.

FIG. 8 is a block diagram illustrating a configuration example of a measuring system in Example 1.

FIG. 9 is a block diagram illustrating a configuration example of an understanding level distinguishing dictionary generating device in Example 1.

FIG. 10 is a flowchart illustrating one example of understanding level distinguishing dictionary generation processing in Example 1.

FIG. 11 is a flowchart illustrating one example of understanding level distinguishing processing in Example 1.

FIG. 12 is one example of an understanding level distinguishing result in Example 1.

FIG. 13 is a flowchart illustrating one example of collation processing of the difficulty level of contents and the understanding level distinguishing result of a user in Example 1

FIG. 14 is one example of the collation result in Example 1.

FIG. 15 is one example of a time synchronization result in Example 1.

FIG. 16 is a flowchart illustrating one example of understanding type distinguishing processing in Example 1.

FIG. 17 is one example of an understanding type result in Example 1.

FIG. 18 is a flowchart illustrating one example of presented information control processing in Example 1.

FIG. 19 is one example of control contents in Example 1.

FIG. 20 is one example of a warning message output to a touch panel in Example 1.

FIG. 21A is one example of a user interface in a case where that the user does not understand a word is an understanding type, in Example 1.

FIG. 21B is one example of a user interface in a case where that the user does not understand a sentence structure is the understanding type, in Example 1.

FIG. 22A is one example of a user interface in a case where that the user does not understand a topic is the understanding type, in Example 1.

FIG. 22B is one example of a user interface in a case where that a speed of voice is high is the understanding type, in Example 1.

FIG. 22C is one example of a user interface in a case where that there is an accent in voice is the understanding type, in Example 1

DESCRIPTION OF EMBODIMENTS

The embodiment describes a conversation system. The conversation system presents information to a user, and calculates an understanding level with respect to the information of the user from bioinformation of the user referring to the information. The conversation system specifies an understanding type which indicates the reason why the user cannot understand the information by collating the calculated understanding level and the difficulty level of the presented information with each other, and controls information to be presented next in accordance with the understanding level and the understanding type.

Example 1

FIG. 1 illustrates a configuration example of the conversation system. A conversation system 101 includes, for example, a conversation device 102, a touch panel 103, and a bioinformation measuring machine 104. The conversation device 102 is configured of a computer including, for example, a processor (CPU) 121, an auxiliary storage device 105, a memory 106, an input/output interface 122, and a communication interface 123.

The processor 121 executes a program accommodated in the memory 106. The memory 106 includes a ROM which is a nonvolatile storage element and an RAM which is a volatile storage element. The ROM accommodates an unchanging program (for example, BIOS) or the like therein. The RAM is a high-speed volatile storage element, such as a dynamic random access memory (DRAM), and temporarily accommodates the program to be executed by the processor 121 and data to be used when executing the program therein.

The auxiliary storage device 105 is a large-capacity nonvolatile storage device, such as a magnetic storage device (HDD) or flash memory (SSD), and accommodates the program to be executed by the processor 121 and the data to be used when executing the program therein.

The input/output interface 122 is an interface which connected with the touch panel 103 or the like, receives an input from an operator or the like, and outputs an execution result of the program in a format that can be visually confirmed by the operator or the like. The touch panel 103 receives a character input and a voice input from the user, and outputs character information and voice information. The input/output interface 122 may be connected with an input device, such as a keyboard, a mouse, and a microphone, and an output device, such as a display device, a printer, and a speaker.

The communication interface 123 is a network interface device which controls the communication with other devices in accordance with predetermined control. In addition, the communication interface 123 includes, for example, a serial interface, such as a USB. The communication interface 123 is connected with, for example, the bioinformation measuring machine 104 which measures the bioinformation of the user. The machine which measures a change in cerebral blood flow amount which is one example of a cerebral function by near-infrared spectroscopy, is one example of the bioinformation measuring machine 104. In addition, the bioinformation measuring machine 104 may obtain, for example, cerebral function information by another measurement method, such as a magnetic field measurement.

The program to be executed by the processor 121 may be provided in the conversation device 102 via a removable media (CD-ROM, flash memory or the like) or network, and may be accommodated in the nonvolatile auxiliary storage device 105 which is a non-temporary storage medium. Therefore, the conversation device 102 may have an interface that reads the data from the removable media.

The conversation device 102 is a computer system which is configured physically on one computer and on a plurality of computers that is theoretically or physically configured, and may be operated by an individual thread on the same computer, or may be operated on a virtual machine constructed on a plurality of physical computer resources.

The auxiliary storage device 105 accommodates, for example, text data 107, voice data 108, and understanding level distinguishing dictionary data 109 therein. The text data 107 includes a plurality of texts. For example, a news article, a book in which the user is interested, textbooks or reference books of each subject at elementary school, middle school, and high school, and the like are one example of each of the texts included in the text data 107. In addition, advertisement contents in marketing or contents advertised by a manager or the like are also one example of each of the texts included in the text data 107. Specific contents of each of the texts included in the text data 107 will be described later.

The voice data 108 includes voice which is associated with each of the plurality of texts included in the text data 107. Each voice included in the voice data includes contents equivalent to the corresponding text. Each voice included in the voice data is, for example, synthesized voice that can adjust the speed and accent. In addition, the conversation device 102 may include a function of newly adding, removing, and editing the text data 107 and the voice data 108 as necessary. The understanding level distinguishing dictionary data 109 accommodates the understanding level distinguishing dictionary generated in understanding level distinguishing dictionary generation processing which will be described later in advance therein. Specific contents of the understanding level distinguishing dictionary will be described later.

The memory 106 includes an information presenting portion 110, a difficulty level analyzing portion 111, a bioinformation obtaining portion 112, an understanding level distinguishing portion 113, a collation portion 114, an understanding type distinguishing portion 115, and an information control portion 116, which are respectively programs.

As the program is executed by the processor 121, the determined processing is performed while using the storage device and a communication port (communication device). Therefore, in the embodiment, the description that uses the program as a subject may be the description that uses the processor 121 as a subject. Otherwise, the processing executed by the program is processing performed by the computer and a computer system in which the program is operated.

The processor 121 is operated as a functional portion (means) which realizes a predetermined function by operating in accordance with the program. For example, the processor 121 functions as an information presenting portion (information presenting means) by operating in accordance with the information presenting portion 110, and functions as a difficulty level analyzing portion (difficulty level analyzing means) by operating in accordance with the difficulty level analyzing portion 111. Other programs are also similar thereto. Furthermore, the processor 121 is also operated as a functional portion (means) which realizes each of the plurality of processing executed by each of the programs. The computer and the computer system are a device and a system including the functional portions (means).

The information presenting portion 110 outputs, for example, contents of the text data 107 and/or the voice data 108 which are selected in accordance with an instruction from the user, to the touch panel 103 as presented information. The contents are configured of a plurality of elements. For example, in a case where the contents are sentence data, each of a plurality of words included in the sentence data is one example of elements of the contents. The bioinformation obtaining portion 112 obtains a time series of bioinformation of the user measured by the bioinformation measuring machine 104 during the understanding activity of the user with respect to the presented information output by the information presenting portion 110.

An understanding activity of the user indicates an activity for understanding the presented information by any of five senses by the user. For example, reading the presented information in a text format by the user and hearing the presented information in a voice format by the user, are one example of the understanding activity of the user. In addition, in the example, the time series of the bioinformation indicates bioinformation at two or more time points. In addition, each of the time series of the bioinformation is made of signal of one or more channels. A brain activity signal is one example of the bioinformation.

The difficulty level analyzing portion 111 analyzes the difficulty level at a presenting time of the contents of the text included in the text data and the contents of the voice included in the voice data. The understanding level distinguishing portion 113 refers to the understanding level distinguishing dictionary included in the understanding level distinguishing dictionary data 109, and calculates the understanding level at each time of the user with respect to the presented information, from the time series of the bioinformation when the user performs the understanding activity with respect to the presented information obtained by the bioinformation obtaining portion 112.

The collation portion 114 collates the understanding level of the user calculated by the understanding level distinguishing portion 113 and the difficulty level of the presented information analyzed by the difficulty level analyzing portion 111 with each other, and synchronizes the time. The understanding type distinguishing portion 115 distinguishes the understanding type of the user based on the time synchronization result of the collation portion 114. The understanding type of the user indicates the reason why the user cannot understand the contents in a case where the user does not understand the contents. The information control portion 116 performs the control of the information presented to the user next based on the understanding type of the user distinguished by the understanding type distinguishing portion 115.

FIG. 2 is one example of the text included in the text data 107. A text 200 is an example of the text of the news article for learning English that regards Japanese user as a target. The text 200 includes, for example, a contents type 201, a background 202, contents 203, and a word interpretation 204. The contents type 201 includes a keyword that indicates the type of the contents of the text 200. In the example of FIG. 2, the contents of the text 200 is written in English about the news of brain science.

The background 202 includes background knowledge of the contents of the text 200. The background 202 may include the background knowledge in a plurality of types of languages. In the example of FIG. 2, the background 202 includes the background knowledge of an English version and a Japanese version. In addition, the background 202 may include image data, such as a picture related to the background knowledge of the contents.

The contents 203 includes a plurality of versions of contents. In the example of FIG. 2, the contents 203 includes the plurality of versions of contents which correspond to a word level or a sentence structure level which is used in contents. In addition, although not particularly illustrated, the contents 203 includes information that indicates the time (for example, time which regards an output start time as a reference) at which the word included in the contents is output via the touch panel 103.

For example, levels are given to each of the versions of the contents in advance such that "Version 1: simple level" indicates contents of which the number of vocabulary words is 1000 or less, "Version 2: intermediate level" indicates contents of which the number of vocabulary words is 1000 or greater and 5000 or less, and "Version 3: advanced level" indicates contents of which the number of vocabulary words is 5000 or greater, in FIG. 2. The word interpretation 204 includes, for example, meaning of a word having a high difficulty level, for example, included in the contents of the corresponding version.

In addition, the difficulty level analyzing portion 111 may give a level to each of the versions of the contents included in the contents 203. The difficulty level analyzing portion 111 gives, for example, a level with reference to a corpus. The corpus is a text format sentence database including, for example, sentences of English textbooks from elementary school to university, English news articles, or the like. The corpus may be accommodated, for example, in the auxiliary storage device 105, or may be accommodated in other computers connected to the conversation device 102.

The difficulty level analyzing portion 111 obtains, for example, a predetermined number or more of sentences from the corpus, sorts the words included in the obtained sentence in an order of high frequency of appearance, and divides a set of sorted words into a plurality of steps by the predetermined number of words. Hereinafter, a step in which the frequency of appearance is low is regarded as a step that corresponds to a high level.

In a case where the predetermined ratio or more of words included in the contents are included in the N-th step and are not included in the N−1-th step, the difficulty level analyzing portion 111 gives the contents a level that corresponds to the N-th step. For example, in a case where a lower limit of the N-th step is 1000 and an upper limit is 2000, the level which corresponds to the N-th step indicates a level of which the number of vocabulary words is 1000 or greater and 2000 or less.

FIG. 3 illustrates one example of information presenting processing performed by the information presenting portion 110. The information presenting portion 110 selects text format contents accommodated in the text data 107 and/or voice format contents which correspond to the contents accommodated in the voice data 108 (S301), in accordance with the input from the user via the touch panel 103.

Specifically, the information presenting portion 110 receives the input of the contents type and the version. The information presenting portion 110 selects the text having the input contents type 201 from the text data 107, and selects the contents of the input version from the contents 203 of the text.

In addition, in a case where a plurality of texts including the input contents type 201 exist, the information presenting portion 110 may randomly select one text from the plurality of texts, may present the plurality of texts to the user, and may select the text in accordance with the input from the user. The information presenting portion 110 obtains the voice format contents which correspond to the selected contents from the voice data 108.

The information presenting portion 110 selects a presenting format of the contents selected in step S301 in accordance with the input from the user via the touch panel 103 (S302). Specifically, for example, the information presenting portion 110 receives input of the information that indicates whether the contents is presented in any one of the text format or the voice format, or in both of the text format and the voice format, and selects the presenting format in accordance with the input information.

Hereinafter, in the example, an example in which the information presenting portion 110 selects both of the text format and the voice format is described, but processing in a case of selecting any one of the text format or the voice format, is also similar to the processing which will be described later. Next, the information presenting portion 110 presents the contents selected in step S301 to the user by outputting the contents to the touch panel 103 in accordance with the time information included in the contents 203 that corresponds to the selected contents, in the presenting format selected in step S302 (S303).

In addition, in step S301 and step S302, the information presenting portion 110 may select the contents and the presenting format, for example, randomly, from the contents included in the text data 107 and/or the contents included in the voice data 108.

FIG. 4 illustrates one example of a contents selection screen which is a user interface for selecting the contents by the user. A contents selection screen 400 includes, for example, a contents type selection section 401, a version selection section 402, and a presenting format selection section 403.

The contents type selection section 401 receives the input of the contents type. In the example of FIG. 4, the user can select the contents type from the subject, the foreign language, the format, and the topic selection, in the contents type selection section 401. In addition, the contents type selection section 401 may receive the input of the contents type by receiving the input of the keyword.

The version selection section 402 receives an input of the version. In the example of FIG. 4, the user can select versions among beginning, intermediate, and advanced versions. The presenting format selection section 403 receives the input of the presenting format selection.

FIG. 4 illustrates an example in which the contents of the intermediate version of the text that includes foreign language, English, news articles, and brain science in the contents type 201 is selected, and the presenting format by the text and the voice is selected, is illustrated. In addition, the information presenting portion 110 may display the contents type of the contents in which the user seems interested on "Recommendation" in the contents type selection section 401, based on the contents selection history by the user.

FIG. 5 illustrates one example of the difficulty level analysis processing of the presented information performed by the difficulty level analyzing portion 111. The difficulty level analyzing portion 111 scores the difficulty level of the text data and the voice data which are presented by the information presenting portion 110.

First, the difficulty level analyzing portion 111 obtains contents presented by the information presenting portion 110 and the output time of each of the words included in the contents, from the information presenting portion 110 (8501). Here, both of the text format contents and the voice format contents are input to the difficulty level analyzing portion 111. The difficulty level analyzing portion 111 determines the difficulty level of the input text format contents and the voice format contents (S502).

The difficulty level analyzing portion 111 determines the difficulty level of the text format contents, for example, by a reference of the word or the sentence structure to be used in the contents. In addition, the difficulty level analyzing portion 111 determines the difficulty level of the voice format contents, for example, by a reference of the speed or the accent of the reproduced contents. A specific example of a difficulty level determining method will be described later. The difficulty level analyzing portion outputs the difficulty level analysis result generated in step S502, and for example, holds the result in the memory 106 (S503).

FIG. 6 is one example of the difficulty level analysis result generated by the difficulty level analyzing portion 111. FIG. 6 is an example of the difficulty level analysis result of the contents of English to be used in English education. A difficulty level analysis result 600 includes, for example, a time 601, a word 602, a word difficulty level 603, a sentence structure difficulty level 604, a speed difficulty level 605, and an accent difficulty level 606. The time 601 indicates, for example, a time at which the corresponding word 602 is displayed on the touch panel 103 as the text, and is output from the touch panel 103 as voice.

The word 602 indicates the word included in the contents. The word included in the word 602 is extracted from the sentence included in the contents by using means, such as morphological analysis, by the difficulty level analyzing portion 111. In addition, the contents included in the text data 107 and the voice data 108 may be divided by a unit of word in advance.

The word difficulty level 603 indicates the difficulty levels of each of the corresponding words 602. Hereinafter, one example of processing for calculating the word difficulty level 603 of each of the words performed by the difficulty level analyzing portion 111 will be described. The difficulty level analyzing portion 111 calculates, for example, frequency (the number of times of appearance of the word in corpus/the total number of words including overlapping in the corpus) of each of the words in the corpus. A value obtained by substituting the frequency calculated by the difficulty level analyzing portion to a predetermined decreasing function of which a range is 0.0 to 1.0 is determined as the word difficulty level 603 of the word. Accordingly, a word having low frequency in the corpus is considered as a word having a high word difficulty level, that is, a difficult word, and a word having high frequency is considered as a word having a low word difficulty level, that is, a simple word.

The sentence structure difficulty level 604 indicates the difficulty level of the sentence structure of each of the corresponding words 602. Hereinafter, one example of processing for calculating the difficulty level of the sentence structure of each of the words performed by the difficulty level analyzing portion 111 will be described. The difficulty level analyzing portion 111 searches for the sentence structure included in each of the words by using the means for analyzing the sentence structure, or the like. Each phrase, a verb phrase, a verb phrase with auxiliary verb, continuative modifier data, adnominal modifier data, unique expression and the like are one example of the sentence structure. There is a case where one word is included in one or more sentence structures, or there is also a case where one word is not included in any of the sentence structures.

The difficulty level analyzing portion 111 calculates the frequency (the number of times of appearance of the sentence structure in corpus/the total number of sentence structures including overlapping in the corpus) of each of the sentence structures including each of the words in the corpus. The difficulty level analyzing portion 111 selects the lowest frequency from the frequency of the sentence structure including the word, for example, with respect to each of the words. A value obtained by substituting the selected frequency to a predetermined decreasing function of which a range is 0.0 to 1.0 is determined as the sentence structure difficulty level 604 of the word. In addition, the difficulty level analyzing portion 111 determines the sentence structure difficulty level 604 of the word which is not included in any of the sentence structures, for example, to 0.0. Accordingly, the word included in a sentence structure having low frequency in the corpus is considered as a word having a high sentence structure difficulty level, and a word having high frequency is considered as a word having a low sentence structure difficulty level.

In addition, the difficulty level analyzing portion 111 may randomly select the frequency, for example, instead of selecting the lowest frequency from the frequency of the sentence structure including the word, or may calculate an average value or the like of the frequency of the sentence structure including the word.

The speed difficulty level 605 indicates the difficulty level according to the speed obtained when the corresponding word 602 is read out aloud as the voice format contents. The speed difficulty level 605 is given, for example, according to separation from the speed of the standard language voice. Hereinafter, one example in which the difficulty level analyzing portion 111 calculates the speed difficulty level 605 of each of the words, will be described.

The difficulty level analyzing portion 111 obtains the words which are the same as those of each of the words, for example, from a voice corpus. The voice corpus is, for example, a voice format sentence database including voice made by reading out aloud the English textbook from the elementary school to the university in standard language, or voice made by reading out aloud the English news articles in standard language. The voice corpus, for example, may be accommodated in the auxiliary storage device 105, or may be accommodated in other computers connected to the conversation device 102.

The difficulty level analyzing portion ill calculates, for example, an average speed of the word which is the same as the word obtained from the voice corpus, and determines the separation from the average speed to the speed of the word, with respect to each of the words. For example, the speed which is lower than the average speed is given as a negative value, and the speed which is higher than the average speed is given as a positive value. The difficulty level analyzing portion 111 determines the determined speed, for example, a value substituted to the predetermined increasing function of which the range is 0.0 to 1.0, to the speed difficulty level 605. Accordingly, a word having a high speed is considered as a word having a high speed difficulty level, and a word having a low speed is considered as a word having a low speed difficulty level.

The accent difficulty level 606 indicates the difficulty level according to the accent obtained when the corresponding word 602 is read out aloud as the voice format contents. Hereinafter, one example of processing for calculating the accent difficulty level 606 of each of the words performed by the difficulty level analyzing Portion 111 will be described. The difficulty level analyzing portion 111 generates, for example, parameters that indicate the accents of each of the words. The difficulty level analyzing portion 111 calculates an average parameter of the accent of the word which is the same as the word obtained from the inside of the voice corpus, and determines an absolute value of the separation from the average parameter to the accent of the word, for example, with respect to each of the words. The difficulty level analyzing portion 111 determines the determined accent, for example, the value substituted to the predetermined increasing function of which the range is 0.0 to 1.0, to the accent difficulty level 606. Accordingly, a word having a large separation from the accent of the standard language is considered as a word having a high accent difficulty level, and a word having a small separation is considered as a word having a low accent difficulty level.

The difficulty level analyzing portion 111 determines the difficulty levels of each of the types of each of the words by the above-described processing. In addition, the difficulty levels of each of the types in the example indicate that an index indicated by the difficulty level of the type becomes difficult as the value increases, and indicates that the index indicated by the difficulty level of the type becomes easy as the value decreases.

FIG. 7 is one example of hemoglobin concentration data which is one example of the bioinformation obtained by the bioinformation obtaining portion 112. The example of the hemoglobin concentration data of FIG. 7 illustrates a time series of an oxygenated hemoglobin concentration and a deoxygenated hemoglobin concentration of the user who performs the understanding activities. For example, a near-infrared spectroscopic measuring device which is one example of the bioinformation measuring machine 104 measures the time series of the oxygenated hemoglobin concentration and the deoxygenated hemoglobin concentration in blood at a plurality of measurement parts of a brain surface layer of the user.

The bioinformation measuring machine 104, for example, may measure the hemoglobin concentration in the entire brain, or may measure the hemoglobin concentration only in a speech area that understands the word or frontal lobe that performs a cognitive activity. The bioinformation measuring machine 104 radiates, for example, a near-infrared ray to a living body. The radiated light is incident on the inside of the living body, and the bioinformation measuring machine 104 detects the light which scattered and absorbed in the living body and is transmitted.

In addition, the bioinformation measuring machine 104 performs the measurement, for example, by using a method for obtaining a change in an intracranial blood flow from the inner state when the user performs the understanding activity described in PTL 1. The bioinformation obtaining portion 112 obtains the hemoglobin concentration measured by the bioinformation measuring machine 104, that is, the hemoglobin concentration when the user performs the understanding activities.

FIG. 8 illustrates a configuration example of the measuring system which measures brain measuring data used in generating the understanding level distinguishing dictionary accommodated in the understanding level distinguishing dictionary data 109. A measuring system 801 includes a measurement managing device 802, a touch panel 803, and a bioinformation measuring machine 804. The measurement managing device 802 is configured of a computer including, for example, a processor (CPU) 821, an auxiliary storage device 805, a memory 806, an input/output interface 822, and a communication interface 823.

The description of each of the touch panel 803, the bioinformation measuring machine 804, the processor (CPU) 821, the auxiliary storage device 805, the memory 806, the input/output interface 822, and the communication interface 823 will be omitted since the description thereof is similar to the description of each of the touch panel 103, the bioinformation measuring machine 104, the processor (CPU) 121, the auxiliary storage device 105, the memory 106, the input/output interface 122, and the communication interface 123.

The memory 806 includes an information presenting portion 811 and a bioinformation obtaining portion 812 which are respectively programs. The auxiliary storage device 805 accommodates, for example, text data 807, voice data 808, and living body data 810 therein. The description of each of the text data 807 and the voice data 808 will be omitted since the description thereof is similar to the description of the text data 107 and the voice data 108. The contents included in the text data 807 and the voice data 808 may be the same as the contents included in the text data 107 and the voice data 108, or may be different from the text data 107 and the voice data 108. The living body data 810 accommodates the bioinformation obtained by the bioinformation obtaining portion 812 therein.

The information presenting portion 811 selects the contents from the text data 807 and/or the voice data 808, for example, in accordance with the instruction from the user, and presents the selected contents to the user via the touch panel 803.

Specifically, for example, the information presenting portion 811 selects the contents that can be excellently understood by the user and the contents that is difficult to be understood, in accordance with the instruction from the user. Accordingly, both of the bioinformation in a state where the user understands the information presented by the bioinformation obtaining portion 812 and the bioinformation in a state where the user does not understand the information, can be obtained. For example, in a case where the user is Japanese, the sentence written by Japanese words of the elementary school level is one example of the contents understood by the user, and a sentence written in foreign language that the user has never learned before is one example of the contents that is difficult to be understood by the user.

The bioinformation obtaining portion 812 may obtain the bioinformation of the user that performs the understanding activities with respect to the presented information presented by the information presenting portion 811 from the bioinformation measuring machine 804, and may be accommodated in the living body data 810 regarding the obtained bioinformation as time series data, for example, by dividing the bioinformation with respect to the contents which is excellently understood by the user and the bioinformation with respect to the contents which is difficult to be understood by the user. In addition, the bioinformation obtaining portion 812 may be accommodated in the living body data 810 by adding an identifier of the user to each piece of the obtained bioinformation.

FIG. 9 illustrates a configuration example of an understanding level distinguishing dictionary generating device which generates the understanding level distinguishing dictionary accommodated in the understanding level distinguishing dictionary data 109. An understanding level distinguishing dictionary generating device 902 is configured of a computer including, for example, a processor (CPU) 921, an auxiliary storage device 905, a memory 906, an input/output interface 922, and a communication interface 923.

The description of each of the processor (CPU) 921, the auxiliary storage device 905, the memory 906, the input/output interface 922, and the communication interface 923 will be omitted since the description thereof is similar to the description of each of the processor (CPU) 121, the auxiliary storage device 105, the memory 106, the input/output interface 122, and the communication interface 123.

The memory 906 includes an understanding level distinguishing dictionary generating portion 911 which is a program. The understanding level distinguishing dictionary generating portion 911 generates the understanding level distinguishing dictionary by using the information accommodated in the living body data 910, and accommodates the generated understanding level distinguishing dictionary in understanding level distinguishing dictionary data 909.

The auxiliary storage device 905 accommodates the understanding level distinguishing dictionary data 909 and living body data 910 therein. The understanding level distinguishing dictionary data 909 generates the understanding level distinguishing dictionary created by the understanding level distinguishing dictionary generating portion 911. The living body data 910 accommodates the bioinformation which is the same as the bioinformation accommodated in the living body data 810 therein in advance. In addition, in the example, the conversation system 101, the measuring system 801, and the understanding level distinguishing dictionary generating device 902, are described as separated systems, but may be one system.

FIG. 10 illustrates one example of understanding level distinguishing dictionary generation processing. The understanding level distinguishing dictionary generating portion 911 obtains the plurality of time series of the bioinformation with respect to the contents that is excellently understood by the user, and the plurality of time series of the bioinformation with respect to the contents that is difficult to be understood by the user, from the living body data 910 (S1001). In the following processing, the understanding level distinguishing dictionary generating portion 911 generates the understanding level distinguishing dictionary from training data generated from the obtained data.

The understanding level distinguishing dictionary generating portion 911 performs preprocessing with respect to the signal of each channel included in each of the time series of the bioinformation obtained in step S1001 (S1002). For example, since a near-infrared light measuring device which is one example of the bioinformation measuring machine 804 performs the measurement in which a non-invasive head part blood circulation measuring method that uses the light is used, a signal associated with a brain activity and information associated with the blood circulation of the entire body caused by a heart rate variability, are included in the signal obtained as the bioinformation.

Therefore, the understanding level distinguishing dictionary generating portion 911 can improve the accuracy of the understanding level distinguishing dictionary by performing the preprocessing for removing noise which is information that is not associated with the understanding level with respect to the contents, with respect to the obtained bioinformation. The understanding level distinguishing dictionary generating portion 911 executes the preprocessing in step S1002 by using an algorithm of a frequency band pass filter, multinominal base line correction, main component analysis, independent component analysis or the like.

Next, the understanding level distinguishing dictionary generating portion 911 extracts only fundamental characteristics necessary for identifying the understanding level from each of the time series of the bioinformation to which the preprocessing is performed (S1003). Specifically, the understanding level distinguishing dictionary generating portion 911 computes a feature vector at one or more sampling times, from the signal of the channel included in the time series, with respect to each of the time series at which the preprocessing is performed in step S1002. Each of the sampling times is, for example, a time having a certain interval determined in advance.

As a computing method of the feature vector, various methods are considered. Hereinafter, an example in which an understanding level distinguishing dictionary generating portion 1011 computes the feature vector at sampling time t from a certain time series of the bioinformation, will be described. In addition, the time when the understanding activity starts is set to be 0.

First, the understanding level distinguishing dictionary generating portion 911 sets a time window including the sampling time t. Here, the understanding level distinguishing dictionary generating portion 911 sets the time from $t-\delta$ to $t+\delta$, with respect to a predetermined positive number $\delta$. The understanding level distinguishing dictionary generating portion 911 cuts out a signal from the time $t-\delta$ to the time $t+\delta$, from the signals of each of the channels included in the time series to which the preprocessing of step S1002 is performed.

The understanding level distinguishing dictionary generating portion 911 computes predetermined fundamental statistics (for example, peak amplitude value, average value, variance, gradient, skewness, kurtosis or the like), from the cut-out signals of each of the channels. The understanding level distinguishing dictionary generating portion 911 selects the signal of a channel having the highest sensitivity based on each of the calculated fundamental statistics. A channel having a high sensitivity indicates a channel which strongly reflects the characteristics of the signal in the time window. An f value of variance, the peak amplitude value, and the gradient are one example of sensitivity. The understanding level distinguishing dictionary generating portion 911 generates, for example, the feature vector which considers the fundamental statistics of one type or more selected channels as an element.

Next, the understanding level distinguishing dictionary generating portion 911 generates the discriminant function by optimizing the parameter of a classification algorithm by using the generated feature vector (S1004). The discriminant function is a function into which the feature vector generated from the time series of the bioinformation during the understanding activity of the user is input at a certain time, and which outputs the understanding level in the understanding activity of the time of the user. In the example, the understanding level is given by a numerical value which is 0 to 1.0, that is, of which the range of the discriminant function is 0 to 1.0. When the value of the understanding level increases, the user understands the contents which are the target of the understanding activity at the time better.

The optimization of the parameter of the classification algorithm in step S1004 indicates, for example, determination of the parameter of the classification algorithm such that the understanding level becomes as high as possible in a case where the feature vector that corresponds to the time series of the bioinformation with respect to the contents which is excellently understood by the user is input, and such that the understanding level becomes as low as possible in a case where the feature vector that corresponds to the time series of the bioinformation with respect to the contents which is difficult to be understood by the user is input.

A support vector machine or linear discriminant analysis based on a maximum-margin principle, sparse logistic regression, logistic regression, non-linear classification algorithm hidden Markov model, neural network and the like are one example of the classification algorithm.

Next, the understanding level distinguishing dictionary generating portion 911 includes the generated discriminant function in the understanding level distinguishing dictionary, and accommodates the understanding level distinguishing dictionary in the understanding level distinguishing dictionary data 909 (S1005). In addition, the understanding level distinguishing dictionary generating portion 911 may compute a class (understood/not understood) including each of the feature vectors by collating the generated feature vector and the generated discriminant function with each other, and may include the correspondence of each of the feature vectors and the class including the feature vector in the understanding level distinguishing dictionary. In addition, the feature vector is included in the class "Understood" in a case where the understanding level that corresponds to the feature vector is equal to or greater than a predetermined value, and the feature vector is included in the class "Not understood" in a case where the understanding level that corresponds to the feature vector is less than the predetermine value.

In addition, the above-described understanding level distinguishing dictionary is a general understanding level distinguishing dictionary which can be employed by an arbitrary user, but the bioinformation, such as a brain measurement result, has a characteristic pattern for each user. Therefore, for example, the understanding level distinguishing dictionary generating portion 911 may create the understanding level distinguishing dictionary for each user in a case where the identifier of the user is Given to the time series of the bioinformation accommodated in the living body data 910. In the understanding level distinguishing processing which will be described later, as the understanding level distinguishing portion 113 calculates the understanding level by using the understanding level distinguishing dictionary for each user, the understanding level having higher accuracy can be obtained.

FIG. 11 illustrates one example of the understanding level distinguishing processing in the conversation system 101. The understanding level distinguishing portion 113 obtains the time series of the bioinformation of the user when the understanding activity with respect to the presented information is performed, from the bioinformation obtaining portion 112 (S1101). The understanding level distinguishing portion 113 performs the preprocessing, for example, by a method similar to step S1002 with respect to the signals of each of the channels included in the time series of the obtained bioinformation (S1102).

The understanding level distinguishing portion 113 extracts only the fundamental characteristics necessary for identifying the understanding level from the time series of the bioinformation to which the preprocessing is performed (S1103). Specifically, the understanding level distinguishing portion 113 generates the feature vectors of each time of the time series of the bioinformation to which the bioinformation is performed, for example by a method similar to step S1003.

The understanding level distinguishing portion 113 substitutes the feature vectors of each time into the discriminant function included in the understanding level distinguishing dictionary accommodated in the understanding level distinguishing dictionary data 109, and calculates the understanding level at each time of the user (S1104). In addition, in a case where the discriminant function for each user is accommodated in the understanding level distinguishing dictionary, it is preferable that the understanding level distinguishing portion 113 uses the discriminant function that corresponds to the user in step S1104. Next, the understanding level distinguishing portion 113, for example, outputs the calculated understanding levels at each time, and holds the output in the memory 106 (S1105).

FIG. 12 is one example of the understanding level distinguishing result. The understanding level distinguishing result of FIG. 12 indicates the understanding levels at each time calculated by the understanding level distinguishing portion 113.

FIG. 13 illustrates one example of collation processing of the difficulty level of the contents and the understanding level distinguishing result of the user by the collation portion 114. The collation portion 114 collates the difficulty level of the voice data analyzed by the difficulty level analyzing portion 111 and the understanding level analyzed by the understanding level distinguishing portion 113 with each other by a time axis, and synchronizes the time (S1301). Next, the collation portion 114 collates the difficulty level of the text analyzed by the difficulty level analyzing portion 111 and the understanding level analyzed by the understanding level distinguishing portion 113 with each other by the time axis, and synchronizes the time (S1302).

In Step S1301 and Step S1302, the collation portion 114, for example, time-synchronizes the difficulty level and the understanding level at every certain time. Next, the collation portion 114 outputs the difficulty level of the time-synchronized voice data, the difficulty level of the text data, and the understanding level, and holds the difficulty levels and the understanding levels, for example, in the memory 106 (S1303).

FIG. 14 is one example of the collation result by the collation portion 114. The collation result indicates the correspondence of the understanding level at each time, the word difficulty level and the sentence structure and the sentence structure difficulty level of the text data presented to the user at each time, and the speed and the accent of the voice data presented to the user at each time.

FIG. 15 illustrates one example of a time synchronization result of the difficulty level of the text, the difficulty level of the voice, and the understanding level. The collation portion 114 collates the understanding level distinguishing result, the difficulty level of the text, and the difficulty level of the voice in each section of a predetermined period, such as 1000 ms, at each time.

FIG. 16 illustrates one example of understanding type distinguishing processing performed by the understanding type distinguishing portion 115. The understanding type distinguishing portion 115 obtains a time synchronization result generated by the collation portion 114 (S1601). For example, in a case where the time at which the understanding level is equal to or lower than a first threshold value exceeds a first ratio of the understanding activity time, the understanding type distinguishing portion 115 refers to the difficulty level information of the text and the difficulty level information of the voice at each time at which the understanding level is equal to or lower than the first threshold value, and determines the understanding type during the understanding activity of the user (S1602). In addition, in a case where the time at which the understanding level is equal to or lower than the first threshold value is equal to or lower than the first ratio of the understanding activity time, the understanding type distinguishing portion 115 determines that the user understands the contents.

Hereinafter, a specific example of the understanding type determination processing of step S1602 will be described. For example, in a case where the understanding level is equal to or lower than 50% at a time which is equal to or lower than 80 percent of the understanding activity time, the understanding type distinguishing portion 115 refers to the difficulty level information of the text and the difficulty level information of the voice at each time in a time group in which the understanding level is equal to or lower than 50%.

For example, in a case where the time of the time group in which the word difficulty level is equal to or higher than a second threshold value exists, the understanding type distinguishing portion 115 determines that a case where the user does not understand the word is included in the understanding type. For example, in a case where the time of the time group in which the sentence structure difficulty level is equal to or higher than a third threshold value exists, the understanding type distinguishing portion 115 determines that a case where the user does not understand the sentence structure is included in the understanding type.

For example, in a case where the time of the time group in which the speed difficulty level is equal to or higher than a fourth threshold value exists, the understanding type distinguishing portion 115 determines that a case where the speed of the voice is high is included in the understanding type. For example, in a case where the time of the time group in which the accent difficulty level is equal to or higher than a fifth threshold value exists, the understanding type distinguishing portion 115 determines that a case where there is an accent in voice is included in the understanding type.

In addition, for example, in a case where the understanding level is equal to or lower than the predetermined threshold value at the time when the understanding activity time is equal to or higher than the second ratio (the second ratio is equal to or lower than the first ratio), the understanding type distinguishing portion 115 determines that a case where the user does not understand the topic of the contents is included in the understanding type.

In addition, in a case where a plurality of understanding types exist, the understanding type distinguishing portion 115 may narrow down the understanding type, that is, the reason why the user cannot understand the contents. For example, priorities are determined in advance for each of the understanding types, and the understanding type distinguishing portion 115 selectively narrows down the plurality of understanding types to a predetermined number of understanding types in accordance with the priority.

In addition, for example, the understanding type distinguishing portion 115 may preferentially determine the priority of each of the plurality of understanding types. When a case where the user does not understand the topic is included in the understanding type, the understanding type distinguishing Portion 115 determines, for example, a value obtained by multiplying a first weight by an average value of the understanding level, as the priority that corresponds to a case where the user does not understand the topic.

When a case where the user does not understand the word is included in the understanding type, the understanding type distinguishing portion 115 preferentially determines a value obtained by multiplying a second weight by an average value of the word difficulty level which is equal to or higher than the second threshold value of the word of which the understanding level is equal to or lower than the first threshold value, corresponding to a case where the user does not understand the word. When a case where the user does not understand the sentence structure is included in the understanding type, the understanding type distinguishing portion 115 preferentially determines, for example, a value obtained by multiplying a third weight by an average value of the sentence structure difficulty level which is equal to or lower than the third threshold value of the word of which the understanding level is equal to or higher than the first threshold value, corresponding to a case where the user does not understand the sentence structure.

When a case where the speed of the voice is high is included in the understanding type, the understanding type distinguishing Portion 115 preferentially determines, for example, a value obtained by multiplying a fourth weight by an average value of the speed difficulty level which is equal to or higher than a fourth threshold value of the word of which the understanding level is equal to or lower than the first threshold value, corresponding to a case where the speed of the voice is high. When a case where there is an accent in voice is included in the understanding type, the understanding type distinguishing portion 115 preferentially determines, for example, a value obtained by multiplying a fifth weight by an average value of the accent difficulty level which is equal to or higher than a fifth threshold value of the word of which the understanding level is equal to or lower than the first threshold value, corresponding to a case where there is an accent in voice.

FIG. 17 illustrates one example of an understanding type result. In the example of FIG. 17, the current understanding type of the user is a case where the user cannot understand the word, and a possibility that the user cannot understand the entire presented information due to a case where the user cannot understand the word, is high. In other words, the information control portion 116 can improve the understanding level of the user by controlling the presented information based on the understanding type.

FIG. 18 illustrates one example of presented information control processing performed by the information control portion 116. The information control portion 116 obtains the understanding type result determined by the understanding type distinguishing portion 115 (S1801). In other words, the understanding type distinguishing Portion 115 further obtains the information that indicates whether or not the user understands the contents, and the understanding type in a case where the user does not understand the contents.

The information control portion 116 determines whether or not the user understands the contents in accordance with the obtained understanding type result (S1802). In a case where it is determined that the user does not understand the contents (S1802: NO), the information control portion 116 controls the presented information in accordance with the understanding type that indicates the understanding type result (S1803), and presents the next information (S1804). A specific example of the next information in step S1804 in a case where the process has passed via step S1803 will be described later. In a case where it is determined that the user understands the contents (S1802: YES), the information control portion 116 presents the next information, for example, additional contents (S1804).

FIG. 19 illustrates one example of control contents in step S1603. The information control portion 116 performs the control processing in accordance with the control contents determined in advance in accordance with the understanding type. In the example of FIG. 19, an example in which the control in a case where the understanding type is the word is "reword by simple words of which the number of vocabulary words is 1000 or less", the control in a case where the understanding type is the sentence structure is "reword by simple sentence structure", the control in a case where the understanding type is the topic is "introduce background knowledge", the control in a case where the understanding type is the speed is "reword slowly", and the control in a case where the understanding type is the accent is "reword by standard language", is illustrated.

FIG. 20 is one example of a warning message which is output to the touch panel 103 by the information control portion 116. The information control portion 116 outputs the warning message of FIG. 20 to the touch panel 103, in a case where it is determined that the user does not understand the contents, for example, in step S1802.

In a case where the user selects a checkbox that corresponds to "as it is", for example, the information control portion 116 presents the information similar to that of step S1804 in a case where the user understands the contents in step S1802.

In a case where the user selects a checkbox that corresponds to "information control", the information control portion 116 performs the control of information to be presented next in accordance with the understanding type, in step S1803. Hereinafter, a specific example of step S1803 and step S1804 by the screen presented to the user and the information control portion 116 in a case where the user selects a checkbox that corresponds to "information control", will be described.

FIG. 21A is one example of a user interface output to the touch panel in step S1803 by the information control portion 116 when a case where the user does not understand the word is the understanding type. The user interface displays, for example, contents that the user does not understand the word and a message that shows a countermeasure, and the text format contents in which the word of which the word difficulty level is equal to or higher than the second threshold value is surrounded by a thick frame. In addition, the word of which the understanding level is equal to or lower than the first threshold value and the word difficulty level is equal to or higher than the second threshold value may be surrounded by the thick frame.

In a case where the user selects a checkbox that corresponds to "meaning of word", for example, the information control portion 116 obtains the meaning of the word surrounded by the thick frame from the word interpretation 204, and outputs the meaning to the touch panel 103. Accordingly, the user can understand the meaning of the word having a low understanding level.

In addition, in a case where the user selects a checkbox that corresponds to "reword by a simple version", for example, the information control portion 116 selects the contents of a version which is simpler than the contents, from the contents 203, and outputs the contents to the touch panel 103.

FIG. 21B is one example of a user interface output to the touch panel in step S1803 by the information control portion 116 when a case where the user does not understand the sentence structure is the understanding type. The user interface displays, for example, contents that the user does not understand the sentence structure and a message that shows a countermeasure, and the text format contents in which the word of which the sentence structure difficulty level equal to or higher than the third threshold value is surrounded by a thick frame. In addition, the word of which the understanding level is equal to or lower than the first threshold value and the sentence structure difficulty level is equal to or higher than the third threshold value may be surrounded by the thick frame.

In a case where the user selects a checkbox that corresponds to "as it is", for example, the information control portion 116 performs processing similar to that of a case where the sentence structure is not included in the understanding type in the next information presenting. In a case where the user selects a checkbox that corresponds to "simple version", the information control portion 116 selects the contents of a version which is simpler than the contents, from the contents 203, and outputs the contents to the touch panel 103.

FIG. 22A is one example of a user interface output to the touch panel in step S1803 by the information control portion 116 when a case where the user does not understand the topic is the understanding type. The user interface displays, for example, contents that the user does not understand the topic and a message that shows a countermeasure, and the text format contents.

In a case where the user selects a checkbox that corresponds to "Japanese", the information control portion 116 selects the background knowledge of the Japanese version of the contents from the background 202, and outputs the background knowledge to the touch panel 103. In a case where the user selects a checkbox that corresponds to "English", the information control portion 116 selects the background knowledge of the English version of the contents from the background 202, and outputs the background knowledge to the touch panel 103. In a case where the user selects a checkbox that corresponds to "picture", the information control portion 116 selects the picture from the background 202 of the contents, and outputs the picture to the touch panel 103.

FIG. 22B is one example of a user interface output to the touch panel in step S1803 by the information control portion 116 when a case where the speed of the voice is high is the understanding type. The user interface displays, for example, contents that the user does not understand the voice since the speed of the voice is high and a message that shows a countermeasure, and the text format contents.

In a case where the user selects a checkbox that corresponds to "as it is", the information control portion 116 performs processing similar to that of a case where the speed is not included in the understanding type in the next information to be presented. In a case where the user selects a checkbox that corresponds to "slowly", the information control portion 116, for example, creates and outputs the voice data of which the speed of all of the words in the presented contents or the word of which the speed difficulty level is equal to or higher than the fourth threshold value, is lowered by a predetermined value or lowered to a predetermined value.

FIG. 22C is one example of a user interface output to the touch panel in step S1803 by the information control portion 116 when a case where there is an accent in voice is the understanding type. The user interface displays, for example, contents that the user does not understand the voice since there is an accent of voice and a message that shows a countermeasure, and the text format contents.

In a case where the user selects a checkbox that corresponds to "as it is", the information control portion 116 performs processing similar to that of a case where the speed is not included in the understanding type in the next information to be presented. In a case where the user selects a checkbox that corresponds to "standard language", the information control portion 116, for example, creates and outputs the voice data of which the separation from the accent of the standard language of all of the words in the presented contents or the word of which the accent difficulty level is equal to or higher than the fifth threshold value, is lowered by a predetermined value or lowered to a predetermined value.

Above, in step S1803, an example in which the information control portion 116 outputs the screen similar to FIGS. 20 to 22C, and the user selects the information in the screen and determines the next information to be presented in accordance with the selected information, is described.

The information control portion 116 may automatically determine any of the information that corresponds to the chec boxes in FIGS. 20 to 22C to the next information to be presented without outputting the screen described in FIGS. 20 to 22C, in step S1803. In addition, for example, when a case where the user does not understand the sentence structure is the understanding type, in a case where the ratio of the words which is occupied by the words in the presented contents and of which the word difficulty level is equal to or higher than the second threshold value, is equal to or higher than the predetermined value, the information control portion 116 may output the meaning of the word of which the word difficulty level is equal to or higher than the second threshold value, or may output the contents of a version which is simpler than the contents.

Above, the conversation system 101 of the example can specify the objective understanding level and understanding type with respect to the presented information of the user with excellent accuracy by collating the bioinformation during the understanding activity of the user with respect to the presented information and the difficulty level of the presented information with each other. In addition, the conversation system 101 of the example has contents similar to the presented information by determining the information to be presented next based on the understanding level and the understanding type, and can present the information in accordance with the understanding level of the user. Specifically, for example, the conversation system 101 can improve the understanding level of the user by presenting the information in which the element having a low understanding level and a high difficulty level of the user is replaced to the element having a low difficulty level.

As described above, since the conversation system 101 can distinguish the understanding level of the user with respect to the presented information, the conversation system 101 can be employed not only in the contents related to the education as described above, but also in advertisement, marketing, and contents of medical field or the like. The contents of these fields may be accommodated in advance in the text data 107 and the voice data 108.

In addition, the memory 106 may not include the voice recognizing portion which performs word recognition by the voice, and for example, instead of receiving the above-described input of the user by the information presenting portion 110 and the information control portion 116, the voice recognizing portion receives the input by a voice word received from the user, and sends the input to the information presenting portion 110 and the information control portion 116. Accordingly, the conversation system 101 can perform conversation with a human by natural language.

In the example, an example in which the information presenting portion 110 selects one or both of the text and voice in selecting the format to be presented in step S302, is described, but in a case where other presenting types of data, such as music, image, or video, is accommodated in the auxiliary storage device 105, other presenting types may be selected.

In addition, the difficulty level analyzing portion 111 of the example analyzes the difficulty level, but may receive a direct input of the difficulty level from the user. For example, by using the conversation system 101, in a case of conducting market investigation regarding the understanding level of a video of an advertisement, as an investigator sets the difficulty level to be high, for example, at a predetermined time of the video, the conversation system 101 can output the understanding type of the investigation target at the predetermined time.

Example 2

In Example 1, an example in which the bioinformation measuring machine 104 and the bioinformation measuring machine 804 use the near-infrared spectroscopy as a brain function measuring method is described, but the bioinformation measuring machine 104 and the bioinformation measuring machine 804 may use a method which is called a brain waves or functional magnetic resonance imaging method.

In addition, the bioinformation measuring machine 104 and the bioinformation measuring machine 804 may further include eye tracking equipment or a camera, and may further observe a sight line or facial expression. At this time, the bioinformation obtaining Portion 112 and the bioinformation obtaining portion 812 further obtain the sight line information and the facial expression information which are recognized by the bioinformation measuring machine 104 and the bioinformation measuring machine 804.

The understanding level distinguishing portion 113 and the understanding level distinguishing dictionary generating portion 911 extract the characteristics from the bioinformation including the sight line information and the facial expression information. Above, the conversation system 101 of the example can obtain a high understanding level with high accuracy.

In addition, the present invention is not limited to the above-described examples, and includes various modification examples. For example, the above-described examples are described in detail for making it easy to describe the present invention, and are not limited to a case where all of the described configurations are necessarily provided. In addition, it is also possible to replace a part of the configuration of a certain example to the configuration of another example, and to add the configuration of another example to the configuration of a certain example. In addition, regarding a part of the configuration of each of the examples, it is possible to add, remove, and replace other configurations.

In addition, a part or the entirety of each of the configurations, functions, processing portions, and processing means which are described above may be realized by hardware, for example, by design or the like of an integrated circuit. In addition, each of the configurations and functions which are described above may interpret the program by which the processor realizes each of the functions, and may be realized by software by the execution. The information of a program, a table, or a file which realizes each of the functions can be placed in a recording device, such as a memory, a hard disk, or a solid state drive (SSD), or a recording device, such as an IC card, an SD card, and a DVD.

In addition, control lines or information lines which are considered as necessary for the description are illustrated, and all of the control lines or information lines which are necessary for a product are not illustrated. In practice, almost all of the configurations may be considered to be connected to each other.

The invention claimed is:

1. A system which controls information presented to a user referring to contents including a plurality of elements, comprising:

a processor;

a storage device; and an output device, wherein the storage device includes the contents, difficulty level information that indicates difficulty levels of each of the plurality of elements, and presented information which corresponds to each understanding type that indicates a reason why the user cannot understand the contents, and wherein the processor outputs a first element that is understood by the user and a second element that is not understood by the user to the output device, obtains first bioinformation of the user referring to the first element and second bioinformation of the user referring to the second element, generates an understanding level distinguishing dictionary that indicates correspondence of the bioinformation and the understanding level of the user, based on training data including the first bioinformation and the second bioinformation, calculates the understanding level of the user with respect to each of the elements included in the contents, based on each piece of the obtained bioinformation and the understanding level distinguishing dictionary, determines the understanding type based on the calculated understanding level and a difficulty level indicated by the difficulty level information of the elements of which the understanding level is equal to or lower than a first threshold value, in a case where it is determined that the user does not understand the contents based on the calculated understanding level, and outputs the presented information which corresponds to the determined understanding type to the output device.

2. The system according to claim 1, wherein the storage device includes a plurality of types of the difficulty level information, selects a first element of which the understanding level is equal to or lower than the first threshold value in a case where it is determined that the user does not understand the contents based on the calculated understanding level, obtains the difficulty level of the selected element, that is, the difficulty level which is equal to or higher than a threshold value that corresponds to the difficulty level information including the difficulty level, from the plurality of types of difficulty level information, selects one or more pieces of difficulty level information from the plurality of types of difficulty level information, based on a comparison result of the obtained difficulty levels, and determines the understanding type based on the selected one or more pieces of difficulty level information.

3. The system according to claim 1, wherein the presented information includes first presented information which is the contents in which each of the elements of a first element group configured of one or more elements of the contents is replaced to an element of which the difficulty level is lower than that of the element, wherein the first presented information corresponds to a first understanding type, and wherein the processor determines whether or not a first condition that the understanding level is equal to or lower than the first threshold value and the difficulty level indicated by the difficulty level information is equal to or higher than a second threshold value is satisfied, with respect to each of the elements of the first element group, in a case where it is determined that the user does not understand the contents, based on the calculated understanding level, and determines the understanding type as the first understanding type in a case where it is determined that all of the elements of the first element group satisfy the first condition.

4. The system according to claim 1, wherein the presented information includes second presented information that indicates background knowledge of the contents, wherein the second presented information corresponds to a second understanding type, and wherein the processor determines the understanding type as the second understanding type in a case where it is determined that the understanding level which takes a predetermined ratio or more in the calculated understanding level is equal to or lower than a third threshold value.

5. The system according to claim 1, wherein the contents include text format sentence data, wherein each of the plurality of elements is a word included in the sentence data, and wherein the difficulty level information indicates at least one of the difficulty level of each word included in the sentence data, and the difficulty level of a sentence structure including each of the words included in the sentence data.

6. The system according to claim 5, wherein the difficulty level information indicates the difficulty levels of each of the words included in the sentence data, wherein the presented information includes third presented information that indicates interpretation of a first word included in the sentence data, wherein the third presented information corresponds to a third understanding type, and wherein the processor determines the understanding type as the third understanding type in a case where it is determined that the user does not understand the contents based on the calculated understanding level, and the understanding level of the first word is equal to or lower than the first threshold value and the difficulty level of the first word is equal to or higher than a fourth threshold value.

7. The system according to claim 5, wherein the difficulty level information indicates the difficulty levels of each of the words included in the sentence data, and wherein the processor obtains text format first sentence data including a plurality of words, and determines the difficulty level of the word based on frequency in the first sentence data of each of the words included in the sentence data.

8. The system according to claim 5, wherein the difficulty level information indicates a difficulty level of the sentence structure including each of the words included in the sentence data, and wherein the processor obtains text format second sentence data including the plurality of words, and determines the difficulty level of the sentence structure including the words based on frequency in the second sentence data of each of the sentence structures including each of the words included in the sentence data.

9. The system according to claim 1, wherein the contents include voice format sentence data, wherein each of the plurality of elements is a word included in the sentence data, and wherein the difficulty level information indicates at least one of a difficulty level of a speed obtained when each of the words included in the sentence data is output to the output device, and a difficulty level of an accent obtained when each of the words included in the sentence data is output to the output device.

10. The system according to claim 9, wherein the difficulty level information indicates the difficulty level of the speed obtained when each of the words included in the sentence data is output to the output device, and wherein the processor obtains voice format third sentence data including the plurality of words, and determines the difficulty level of the speed obtained when each of the words included in the sentence data is output to the output device, based on a comparison result of the speed obtained when each of the words included in the sentence data is output to the output device and the speed obtained when the word included in the third sentence data is output to the output device.

11. The system according to claim 9, wherein the difficulty level information indicates the difficulty level of the accent obtained when each of the words included in the sentence data is output to the output device, and wherein the processor obtains voice format fourth sentence data including the plurality of words, and determines the difficulty level of the accent obtained when each of the words included in the sentence data is output to the output device, based on a comparison result of the accent obtained when each of the words included in the sentence data is output to the output device and the accent obtained when the word included in the fourth sentence data is output to the output device.

12. The system according to claim 1, wherein the bioinformation includes brain function information, sight line information, and facial expression information.

13. A method for controlling information presented to a user referring to contents including a plurality of elements by a system including an output device, wherein the system includes the contents, difficulty level information which indicates a difficulty level of each of the plurality of elements, and presented information which corresponds to each understanding type that indicates a reason why the user cannot understand the contents, and wherein the system outputs a first element that is understood by the user and a second element that is not understood by the user to the output device, obtains first bioinformation of the user referring to the first element and second bioinformation of the user referring to the second element, generates an understanding level distinguishing dictionary that indicates correspondence of the bioinformation and the understanding level of the user, based on training data including the first bioinformation and the second bioinformation, calculates the understanding level of the user with respect to each of the elements included in the contents, based on each piece of the obtained bioinformation and the understanding level distinguishing dictionary, determines the understanding type based on the calculated understanding level and a difficulty level indicated by the difficulty level information of the elements of which the understanding level is equal to or lower than a first threshold value, in a case where it is determined that the user does not understand the contents based on the calculated understanding level, and outputs the presented information which corresponds to the determined understanding type to the output device.

* * * * *